US008163731B2

(12) United States Patent
Slater et al.

(10) Patent No.: US 8,163,731 B2
(45) Date of Patent: Apr. 24, 2012

(54) METHOD AND DOSAGE REGIMENS FOR ELIMINATING A CHEMICAL SUBSTANCE IN BLOOD

(75) Inventors: Kenneth C. Slater, Manchester, MA (US); Brenda E. Richardson, Manchester, MA (US); Scott M. Connors, Methuen, MA (US); Wei-wei Chang, Boston, MA (US)

(73) Assignee: Rhodes Technologies, Coventry, RI (US)

( * ) Notice: Subject to any disclaimer, the term of this patent is extended or adjusted under 35 U.S.C. 154(b) by 477 days.

(21) Appl. No.: 12/195,143

(22) Filed: Aug. 20, 2008

(65) Prior Publication Data

US 2010/0048535 A1 Feb. 25, 2010

(51) Int. Cl.
*A61K 31/485* (2006.01)
*A61K 31/554* (2006.01)
*A61K 31/4709* (2006.01)

(52) U.S. Cl. ..................... 514/211.13; 514/282; 514/305
(58) Field of Classification Search ............. 514/211.13, 514/282, 305
See application file for complete search history.

(56) References Cited

U.S. PATENT DOCUMENTS 6,277,384 B1 * 8/2001 Kaiko et al. .................. 424/400
7,172,767 B2 2/2007 Kaiko et al.

FOREIGN PATENT DOCUMENTS

CA 2621575 A1 8/2008

OTHER PUBLICATIONS

Abramowitz, M.(Editor). Buprenorphine:An Alternative to Methadone.The Medical Letter, (2003),13-15,vol. 45, (Issue W1150A)Feb. 17.
Azar, M.R.et al. A Non-invasive gating device for continuous drug delivery that allows control over the timing and duration of spontaneous opiate withdrawal. J.Neurosci.Methods,(May 30, 2004),129-35,vol. 135 (1-2).
Barnett, P.G. et al. Research Report.A Meta-Analysis Comparing Buprenorphine to Methadone for Treatment of Opiate Dependence. Addiction(2001),683-690,vol. 96.
Barnett, P.G. et al. The Cost-effectiveness of buprenorphine maintenance therapy for opiate addiction in the United States.Addiction(2001),1267-1278,V96.

(Continued)

*Primary Examiner* — Brandon Fetterolf
*Assistant Examiner* — Kathrien Cruz
(74) *Attorney, Agent, or Firm* — Brinks Hofer Gilson & Lione

(57) ABSTRACT

A method of reducing the concentration of a chemical or drug substance in the blood plasma that targets the same or similar receptors as the normal neurotransmitters in the central or peripheral nervous system includes titrating an initial peak concentration of the chemical or drug substance in the blood for a predefined dosing period, titrating a lowest concentration level of the chemical or drug substance in the blood immediately before the end of the dosing period, and providing a plurality of subsequent dosing periods where each subsequent dosing period requires administration of a dosing amount of the chemical or drug substance and titrating of the peak concentration and the lowest concentration level to ensure that the lowest concentration level of the chemical or drug substance in the blood plasma for the subsequent dosing period is decreased by not more than five percent of the lowest concentration level of the previous dosing period and where the plurality of dosing periods added together extends the method for seventy days or more.

12 Claims, 4 Drawing Sheets

OTHER PUBLICATIONS

Becker, A.B. et al. Gradual Dose Taper Following Chronic Buprenorphine.American Journal of Addictions. (2001),111-121,vol. 10.
Bickel, W.K. et al. Buprenorphine dosing every 1,2 or 3 Days in opioid-dependent patients.Psychopharmacology (1999)111-11,vol. 146.
Breen, C.L. et al. Cessation of methadone maintenance treatment using buprenorphine:transfer from methadone to buprenorphine and subsequent buprenorphine reductions. Drug and Alcohol Dependence (2003),49-55,vol. 71.
Calsyn,D.A. et al. Slow Tapering From Methadone Maintenance in a Program Encouraging Indefinite Maintenance. Journal of Substance Abuse Treatment (2006),159-163,vol. 30.
Caplehorn, J. Comments on Mattick et al:The Need for Independent Data Reanalyses. Addiction (2000) 1633-1634, vol. 98.
Chawarski, M.C. et al. Buprenorphine Tablet Versus Liquid: A Clinical Trial comparing Plasma Levels, Efficacy, and Symptoms.Journal of Substance Abuse Treatment.(2005),307-312.
Fiellin, D.A & O'Connor, P.G. New Federal Initiatives to Enhance the Medical Treatment of Opioid Dependence. Annals of Internal Medicine(2002),688-692,vol. 137.
Fiellin, D.A. et al. Counseling Plus Buprenorphine-Naloxone Mainetenance Therapy for Opioid Dependence. The New England Journal of Medicine(2006),365-374,vol. 355.
Law, F.D. et al. The Clinical use of Buprenorphine in Opiate Addiction:Evidence and Practice. Acta Neuropsychiatrica, (2004),246-274, vol. 16.
Litten,R.Z & Allen, J.P. Medications for Alcohol, Illicit Drug, and Tobacco Dependence.An Update of Research Findings. Journal of Substance Abuse Treatment (1999) 105-112 vol. 16,No. 2.
Mahowald, M.L. Opioid use by Patients in an Orthopedics Spine Clinic.Arthritis and Rheumatism (2005),312-321, vol. 52.
Marsch, L.A. et al. Comparison of Pharmacological Treatments for Opioid-Dependent Adolescents: A Randomized Controlled Trial. Archives of General Psychiatry.(2005),1157-116 vol. 62.
Mattick, R.P., et al. Buprenorphine versus Methadone Maintenance Theralpy: A Randomized Double-Blind Trial With 405 Opioid Dependent Patients.Addiction(2003),441-452,vol. 98.
O'Connor, P.G. Methods of Detoxification and Their Role in Treating Patients with Opioid Dependence.JAMA (2005), 961-963,vol. 294.
O'Connor, P.G. et al. Three Methods of Opioid Detoxification in a Primary Care Setting. Ann Inter.Med. (1997), 526-530 vol. 127.
Phillips, G.T. & Bradley, B. The Influence of Psychological Factors on the Opiate Withdrawal Syndrome. British Journal of Psychiatry(1986), 235-238, vol. 149.
Raisch, D.W. et al. Opioid Dependence Treatment,Including Buprenorphine/Naloxone.AnnPharmacother (2002) 312-321 vol. 36.
Raistrick, D.et al. A Comparison of Buprenorphine and Lofexidine for Community Opiate Detoxification: Results From a Randomized Controlled Trial. Addiction 92005) 1860-1862 vol. 100.
Rosenblatt ,A.B & Nagy ,A.M. Management of Pain in Addicted/Illicit and Legal Substance Abusing Patients.Pain Practice.(2005), 2-10,vol. 5,No. 1.
Schottenfeld, R.S. et al. Thrice Weekly Versus Daily Buprenorphine Maintenance. Biol.Psychiatry (2000),1072-1079,vol. 47.
Simpson, D.D. et al. Drug Abuse Treatment Process Components that Improve Retention. Journal of Substance Abuse Treatment. (1997),565-572,vol. 14 No. 6.
Strain, E.C. et al. Buprenorphine Versus Methadone in the Treatment of Opioid Dependence: Self Reports, Urinanalysis, and Addiction Severity Index. Journal of Clinical Psychopharmacology. (Feb. 1996) 58-67 vol. 16 No. 1.
Strang, J and Gossop, M. Comparison of Linear versus Inverse Exponential Methadone Reduction Curves in the Detoxification of Opiate Addicts. Addictive Behavior. (1990), 541-547, vol. 15.
Camarasa, X. et al. Naltrexone-assisted rapid methadone discontinuation: A Pilot Study, European Addition Research, 2007, vol. 13, pp. 20-24.
Strain, E. C. et al. Relative bioavailability of different buprenorphine formulations under chronic dosing conditions, Drub and Alcohol Dependence, 2004, vol. 74, pp. 37-43, Elsevier.
Gilson, A. M., et al., A Reassessment of Trends in the Medical use and Abuse of Opioid Analgesics and Implications for Diversion Control: 1997-2002, Journal of Pain and Symptom Management, 2004, vol. 28, No. 2.
Miller, N. S. and Greenfield, A., Patient Characteristics and Risks Factors for Development of Dependence on Hydrocodone and Oxycodone, American Journal of Therapeutics, 2004, vol. 11, pp. 26-32.
Application for Inclusion of Buprenorphine in the WHO Model List of Essential Medicines, WHO: Department of Mental Health and Substance Abuse, 2004, 1-49.
ACT Methadone Treatment Guidelines, ACT Health, 2003, 1-102.
Bickel, Warren K. et al., "Buprenorphine Treatment of Opioid Dependence: A Review," Experimental and Clinical Psychopharmacology, 1995, pp. 477-489, 3(4), American Psychological Association, Inc., US.
Bickel, Warren K. et al., "Effects of Adding Behavioral Treatment to Opioid Detoxification with Buprenorphine," Journal of Consulting and Clinical Psychology, 1997, pp. 803-810, 65(5), American Psychological Association, Inc., US.
Johnson, Rolley E. et al., "Buprenorphine: how to use it right," Drug and Alcohol Dependence, 2003, pp. S59-S77, 70, Elsevier Science Ireland, Ltd.
Kuhlman, James J., Jr. et al., "Relationship of plasma buprenorphine and norbuprenorphine to withdrawal symptoms during dose induction, maintenance and withdrawal from sublingual buprenorphine," Addiction, 1998, pp. 549-559, 93 (4), Society for the Study of Addiction to Alcohol and Other Drugs, Carfax Publishing Limited.
Wolff, Kim et al., "Methadone Concentrations in Plasma and Their Relationship to Drug Dosage," Clinical Chemistry, 1991, pp. 205-209, 37(2).
European Search Report, European Application No. EP 09 16 8344.
Johnson, Rolley E. et al., Buprenorphine: how to use it right, Drug and Alcohol Dependence, 70 (2003), pp. S59-S77.
Becker, Ami B. et al., Gradual Dose Taper Following Chronic Buprenorphine, the American Journal on Addiction, 10 (2001), pp. 111-121.
Amass, Leslie et al., A Preliminary Investigation of Outcome Following Gradual or Rapid Bupronerphine Detoxification, Journal of Addictive Diseases, vol. 13, No. 3, 1994, pp. 33-45.
Bickel, Warren K. et al., Effects of Adding Behavioral Treatment to Opioid Detoxification With Buprenorphine, Journal of Consulting and Clinical Psychology, American Psychological Association, vol. 65, No. 5, 1997, pp. 803-810.

* cited by examiner

METHOD AND DOSAGE REGIMENS FOR ELIMINATING A CHEMICAL SUBSTANCE IN BLOOD

BACKGROUND OF THE INVENTION

1. Field of the Invention

The present invention relates generally to chemical or drug substances in the blood as they relate to physical dependence. The present invention relates to a method and dosages for controlling the elimination of a chemical or drug substance in blood in order to eliminate physical dependence to these and related chemicals or drug substances.

2. Description of the Prior Art

There are numerous legal and illegal chemical or drug substances currently available in the marketplace. Certain types of chemical or drug substances that are taken repeatedly cause the body to develop a physical dependence for the chemical or drug substance. This physical dependence for some of chemicals and drug substances is called an addiction. Discontinuation of the substance by an individual who has developed a physical dependence for the chemical or drug substance typically causes untoward withdrawal symptoms in the individual.

Examples of chemical or drug substances that can lead to physical dependence include alcohol, opioids (morphine, codeine, thebaine, hydromorphone, hydrocodone, oxycodone, oxymorphone, desomorphine, diacetylmorphine or heroin, nicomorphine, dipropanoylmorphine, benzylmorphine, ethylmorphine, fentanyl, pethidine, methadone, tramadol, propxyphene), amphetamines and derivatives such as MDMA (3,4-Methylenedioxy-N-methamphetamine) and methamphetamine, barbiturates (allobarbital, amobarbital, aprobarbital, alphenal, barbital, brallobarbital, Phenobarbital), benzodiazepines both hypnotic (estazolam, flurazepam, midazolam, triazolam, temazepam, nimetazepam, brotizolam, flunitrazepam, loprazolam, lormetazepam, and nitrazepam), and anxiolytic (alprazolam, chlordiazepoxide, clonazepam, clorazepate, diazepam, lorazepam, oxazepam, prazepam, and bromazepam), gamma-hydroxybutyric acid, methaqualone, cocaine, anticonvulsants (acetazolamide, carbamazepine, clobazam, clonazepam, diazepam, divalproex sodium, ethosuximide, ethotoin, felbamate, fosphenytoin, gabapentin, lamotrigine, levetiracetam, mephenytoin, metharbital, methsuximide, methazolamide, oxycarbazepine, Phenobarbital, phenytoin, phensuximide, pregabalin, primidone, valproic acid, stiripentol, tiagabine, topiramate, trimethadione, vigabatrin, and zonisamide); mood stabilizers (lithium salts, valproic acid, divalproex sodium, sodium valproate, lamotrigine, carbamazepine, gabapentin, oxcarbazepine, and topiramate), antipsychotics (first generation—butyrophenones such as haloperidol, phenothiazines such as chlorpromazine, fluphenazine, perphenazine, thioridazine, trifluoperazine, mesoridazine, promethazine, triflupromazine, and levomepromazine, thioxanthenes such as chlorprothixine, thiothixene, flupenthixol, and zuclopenthixol); second generation—clozapine, olanzapine, risperidone, quetiapine, ziprasidone, amisulpride, paliperidone, and derivatives; third generation—aripiprazole; and others such as tetrabenazine and cannabinoids; antidepressants (serotonin-norepinephrine reuptake inhibitors—SSRIs—include fluoxetine, paroxetine, escitalopram, citalopram, and sertraline; serotonin-norepinephrine reuptake inhibitors—SNRIs—include venlafaxine and duloxetine; noradrenergic and specific serotonergic antidepressnats—NASSAs—such as mirtazapine; norepinephrine reuptake inhibitors—NRIs—such as reboxetine; norepinephrine-dopamine reuptake inhibitors such as bupropion; tricyclic antidepressants—TCAs—such as amitriptyline, imipramine, desipramine, trazodone, and nortriptyline; monoamine oxidase inhibitors—MAOIs—such as phenelzine, moclobenmide; buspirone); methylxanthines such as caffeine, theophylline, and theobromine; nicotine; methylphenidate; and other drugs that act on the nervous systems either central or peripheral, or both. Other chemical or drug substances that do not primarily act on the central nervous system can also cause withdrawal, including antihypertensives in particular beta blockers, and glucosteroids.

For many of these chemicals and drug substances, the central nervous system effects are more noticeable. They act by preventing the uptake of the normal neurotransmitters such as dopamine, serotonin and norepinephrine, and establish new pathways for neurotransmission and cellular function. The peripheral nervous system, however, is also affected, involving disparate parts of the body such as the heart or gastrointestinal system.

Following repeated exposure on a prolonged basis, the body systems develop physical dependence by adapting to the uptake of the administered chemical or drug substances as they seek new conditions of homeostasis. When abrupt change to the new homeostasis occurs, unpleasant and sometimes life threatening withdrawal symptoms accompany rapid cessation in dosing. Withdrawal symptoms may include dizziness, light-headedness, vertigo or feeling faint, shock-like sensations or paresthesia, anxiety, diarrhea, fatigue, instability, headache, insomnia, irritability, nausea or vomiting, palpitations, tremor, and visual disturbances. Craving in the case of addictive chemical or drug substances can occur either earlier or later following cessation of intake. More serious withdrawal effects may include convulsions, hallucinations, catatonia, coma, suicidal tendencies, hyperthermia, violence, and psychosis. Fatality may occur under certain situations such as mediated by cardiac arrest.

To be more precise, neurotransmitters are various chemical substances that include monoamines (dopamine, epinephrine, norepinephrine, serotonin, and melatonin), amino acids (glutamic acid, gamma aminobutyric acid, aspartic acid and glycine), peptides (vasopressin, somatostatin, etc.), and others such as adenosine, histamine, etc., that through binding to receptors mediate neurotransmission. When chemical or drug substances that cause physical dependence competitively bind to specific receptors, accumulation of specific neurotransmitters can occur. For instance, dopamine levels can increase in the nucleus accumbens, and cause the euphoria associated with opiate use. The usual doses of chemical or drug substances may saturate the receptors. After extended periods of repeated dosing, a sudden withdrawal of the chemical or drug substance can deplete the neurotransmitters that had been released, and precipitate the withdrawal symptoms.

Traditional methods for treatment of dependence involve either very rapid tapering of the drug substance, e.g. nicotine transdermal patches (Habitrol) for smoking cessation or through replacement therapy, e.g. methadone and buprenorphine (Suboxone®/Subutex®), at sustained relatively high doses.

Conventional therapies for opioid addiction treatment are replacement therapies using other opioid agonists. Methadone and buprenorphine replacement therapies are typically aimed at maintenance therapy, not at total cessation. As an example, patients in maintenance treatment with methadone should be titrated to a dose at which opioid symptoms are prevented for 24 hours, drug hunger or craving is reduced, the euphoric effects of self-administered opioids are blocked or attenuated, and the patient is tolerant to the sedative effects of methadone. Most commonly, clinical stability is achieved at doses between 80 to 120 mg/day.

In the case of buprenorphine, the goal is to achieve an optimal maintenance dose. The steps include adjusting the dose until the maintenance dose is achieved. The recommended target dose of Suboxone® is 16 mg/day. Clinical studies have shown that 16 mg of Subutex® or Suboxone® is a clinically effective dose compared with placebo and indicate that doses as low as 12 mg/day may be effective in some patients. The dosage of Suboxone® should be progressively adjusted in increments/decrements of 2 mg or 4 mg to a level that holds the patient in treatment and suppresses opioid withdrawal effects. This is likely to be in the range of 4 mg to 24 mg per day depending on the individual.

Although it has been recognized by many that one way to prevent withdrawal symptoms is through tapering the patient off the medication that led to the physical dependence in the first place, the practice is variable and usually deficient. Examples of inadequacies in the current state of practice of tapering will now be described.

Treatment for alcohol withdrawal is not based on the tapering concept at all, but is designed to treat the side effects which can be fatal. For instance, benzodiazapines are the first line treatment for delirium tremens, with addition of phenobarbital or propofol should the former not be effective.

A survey on the actual practice of tapering shows that the instructions are either absent or vague or that tapering is done in such large decrements that they cause sudden blood level changes.

For serotonin and norepinephrine reuptake inhibitors such as venaflexane, a gradual reduction in the dose rather than abrupt cessation is recommended whenever possible. If intolerable symptoms occur following a decrease in the dose or upon discontinuation of treatment, then the recommendation is to resume the previously prescribed dose. In fact, the instructions state that symptoms associated with discontinuation of Effexor XR®, other SNRIs, and SSRIs, have been reported. Patients should be monitored for these symptoms when discontinuing treatment. In clinical trials with Effexor XR®, tapering was achieved by reducing the daily dose by 75 mg at 1 week intervals, however, individualization of tapering may be necessary.

For paroxetine, the instructions for the discontinuation of treatment with Paxil® state that recent clinical trials supporting the various approved indications for Paxil® employed a taper-phase regimen, rather than an abrupt discontinuation of treatment. The taper-phase regimen used in GAD and PTSD clinical trials involved an incremental decrease in the daily dose by 10 mg/day at weekly intervals. When a daily dose of 20 mg/day was reached, patients were continued on this dose for 1 week before treatment was stopped.

Furthermore, there is a trial and error mode in methods to be used to avoid withdrawal. For paroxetine, the instructions for the discontinuation of treatment with PAXIL C® state that symptoms associated with discontinuation of immediate-release paroxetine hydrochloride or PAXIL CR® have been reported and further instruct to see the precautions. The instructions go on to state that patients should be monitored for these symptoms when discontinuing treatment, regardless of the indication for which PAXIL CR® is being prescribed. Like serotonin and norepinephrine reuptake inhibitors, gradual reduction in the dose of paroxetine rather than abrupt cessation is recommended whenever possible. If intolerable symptoms occur following a decrease in the dose or upon discontinuation of treatment, then resuming the previously prescribed dose may be considered. Subsequently, the physician may continue decreasing the dose but at a more gradual rate. Likewise for sertraline hydrochloride, the instructions state a gradual reduction in the dose rather than abrupt cessation is recommended whenever possible. If intolerable symptoms occur following a decrease in the dose or upon discontinuation of treatment, then resuming the previously prescribed dose may be considered. Subsequently, the physician may continue decreasing the dose but at a more gradual rate.

For amphetamines, there is no current stated practice of dealing with physical dependence.

For benzodiazepines such as Chlorazepate, the instructions state that after extended therapy, abrupt discontinuation of Clorazepate should generally be avoided and a gradual dosage tapering schedule followed.

For methadone, the official prescribing information states that there is considerable variability in the appropriate rate of methadone taper in patients choosing medically supervised withdrawal from methadone treatment. It is generally suggested that dose reductions should be less than 10% of the established tolerance or maintenance dose, and that 10 to 14-day intervals should elapse between dose reductions. The information further states that patients should be apprised of the high risk of relapse to illicit drug use associated with discontinuation of methadone maintenance treatment.

For buprenorphine, the official prescribing information states the following regarding reducing dosage and stopping treatment: The decision to discontinue therapy with Suboxone® or Subutex® after a period of maintenance or brief stabilization should be made as part of a comprehensive treatment plan. Both gradual and abrupt discontinuations have been used, but no controlled trials have been undertaken to determine the best method of dose taper at the end of treatment.

For fentanyl, the official prescribing information states the following for the discontinuation of DURAGESIC®. For patients requiring discontinuation of opioids, a gradual downward titration is recommended since it is not known at what dose level the opioid may be discontinued without producing the signs and symptoms of abrupt withdrawal.

For smoking cessation using nicotine, very large reduction steps are recommended. The resultant clinical success rates are low, at 6-12% over placebo.

Therefore, what is needed is a tapering system that provides for the complete cessation of any chemical or drug substance without the occurrence of withdrawal symptoms.

SUMMARY OF THE INVENTION

It is an object of the present invention to provide a chemical or drug substance tapering system that provides for complete cessation of and dependence on a chemical or drug substance. It is another object of the present invention to provide a chemical or drug tapering system that provides a success rate of 70% or greater. It is a further object of the present invention to provide a plurality of dosages in decrements over a sufficient time period that provides for complete cessation of and dependence on a chemical or drug substance.

The present invention achieves these and other objectives by providing an effective treatment to achieve cessation of chemical or drug use. The present invention requires very gradual lowering of the blood levels for an extended period, e.g. 90-120 days or more. The extended period is required to ensure that the decrease in the lowest blood level from the previous lowest blood level cannot be more than 5%. Otherwise, a more rapid decrease in chemical or drug blood levels will not allow the brain and body to adapt to a new homeostasis without untoward symptoms.

One embodiment of the present invention includes a method of reducing the concentration of a chemical or drug substance in the blood that targets the same or similar receptors as the normal neurotransmitters in the central or peripheral nervous system to a level that no longer interferes with the normal neurotransmitters and their receptors. The method includes titrating an initial peak concentration of the chemical or drug substance in the blood for a predefined dosing period, titrating a lowest concentration level of the chemical or drug substance in the blood immediately before the end of the dosing period to determine the lowest concentration level of the chemical or drug substance, and providing a plurality of subsequent dosing periods wherein each subsequent dosing period requires administration of a dosing amount of the chemical or drug substance to ensure that the lowest concentration level of the chemical or drug substance in the blood plasma for the subsequent dosing period is decreased by not more than five percent of the lowest concentration level of the previous dosing period and wherein the plurality of dosing periods added together extends the method for seventy days or more.

In another embodiment of the present invention, the method includes a stabilizing concentration of the chemical or drug substance in the blood plasma when using a replacement chemical or drug substance instead of using the original chemical or drug substance.

In still another embodiment of the present invention, the method includes selecting a chemical or drug substance that is the original chemical or drug substance or compounds that are agonists for the same receptor sites as the original chemical or drug substance.

In yet another embodiment of the present invention, the method includes a plurality of subsequent dosing periods that, when added together, extends the method for ninety days or more or one hundred twenty days or more.

A further embodiment of the present invention includes a kit for reducing the concentration of a chemical or drug substance in the blood plasma that targets the same or similar receptors as the normal neurotransmitters in the central or peripheral nervous system. The kit includes a plurality of dosage forms of the chemical or drug substance packaged in a plurality of decreasing dosing series where each dosing series defines a dosing period. Each dosing period contains a dosing amount of the chemical or drug substance that when administered ensures that the lowest concentration level of the chemical or drug substance in the blood plasma for the subsequent dosing period is decreased by not more than five percent of the lowest concentration level in the blood plasma of the previous dosing period. The quantity of dosage forms is sufficient for administration for seventy days or more.

In still another embodiment of the present invention, the chemical or drug substance in the kit is selected from the group consisting of the original chemical or drug substance in the blood plasma and compounds that are agonists for the same receptor sites wherein the compounds are used as a replacement chemical or drug substance for the original chemical or drug substance in the blood plasma.

In yet another embodiment of the present invention, the plurality of dosage forms in the kit includes one or more dosage forms of the replacement chemical or drug substance to stabilize the concentration of the replacement chemical or drug substance in the blood plasma before administration of the plurality of subsequent decreasing dosing series.

In another embodiment of the present invention, the quantity of dosage forms in the kit is sufficient for administration for ninety days or more or one hundred twenty days or more.

Another embodiment of the present invention includes a plurality of dosing regimens formulated for reducing the concentration of a chemical or drug substance in the blood plasma that targets the same or similar receptors as the normal neurotransmitters in the central or peripheral nervous system. The plurality of dosing regimens includes a quantity of a chemical or drug substance contained in each of the plurality of dosing regimens where the plurality of dosing regimens includes an initial dosing regimen and a plurality of subsequent dosing regimens. Each dosing regimen defines a dosing period and each dosing period contains a dosing amount of the chemical or drug substance that when administered ensures that the lowest concentration level of the chemical or drug substance in the blood plasma for a subsequent dosing period is decreased by not more than five percent of the lowest concentration level in the blood plasma of a previous dosing period. The quantity of the chemical or drug substance is sufficient for administration for seventy days or more.

In another embodiment of the present invention, the chemical or drug substance of the plurality of dosing regimens is selected from the group consisting of the original chemical or drug substance in the blood plasma and compounds that are agonists for the same receptor sites where the compounds are used as a replacement chemical or drug substance for the original chemical or drug substance in the blood plasma.

In still another embodiment of the present invention, the quantity of the chemical or drug substance in the plurality of dosing regimens includes one or more dosing regimens of the replacement chemical or drug substance to stabilize the concentration of the replacement chemical or drug substance in the blood plasma before administration of the plurality of subsequent dosing regimens.

In yet another embodiment of the present invention, the quantity of the chemical or drug substance in the plurality of dosing regimens is sufficient for administration for ninety days or more or one hundred twenty days or more.

DETAILED DESCRIPTION OF THE PREFERRED EMBODIMENT

Figure 1:
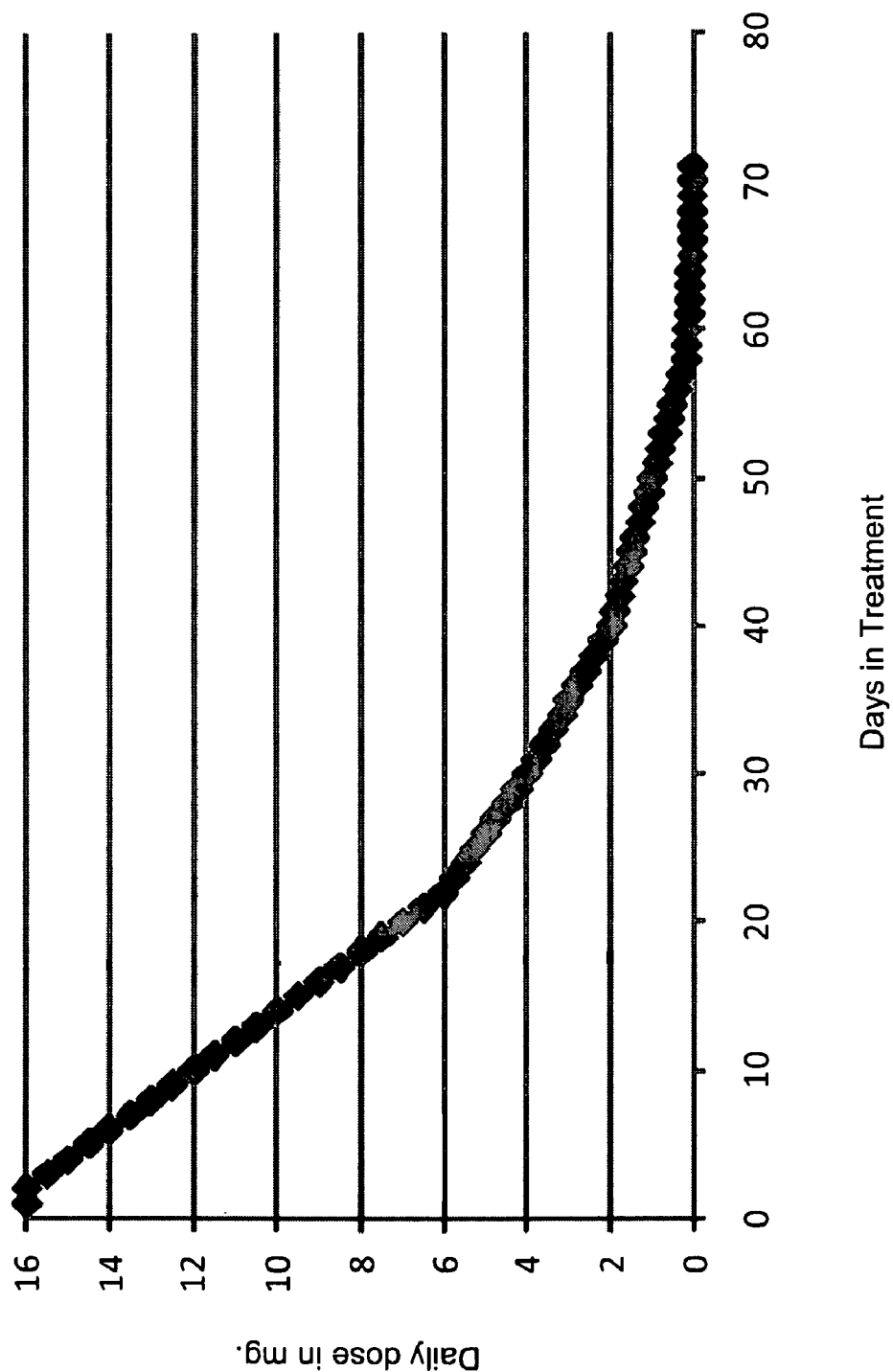
FIG. 1 is a graphic illustration of the actual dosage regimen data for example 5 for an approximate 70 day regimen.

Dependence on psychoactive substances such as opioid drugs has been a major health issue across the globe for many years. Among users, there is an increase in the transmission of HIV and Hepatitis C, which, in effect, increases health care costs for the user but also for the community they effect.

A person can become dependent on psychoactive substances with regular drug use in two manners, physically and psychologically. Physically, the brain becomes used to or adapts to the presence of the drug in order to function "normally". Psychoactive drugs affect the central nervous system and alter what the brain considers normal function. At the beginning of drug use, the user may experience a euphoria because the drug affects the nucleus accumbens, or the brain's "pleasure center". Neurons in the nucleus accumbens use the same neurotransmitter as dopamine, although each drug affects this area differently, drugs either stimulate dopamine release or enhance its activity, directly or indirectly. Initially the body only needs a minimal amount of a substance to function normally and attain the state of euphoria, however, over time and with chronic use, the body builds a tolerance for the drug and therefore needs more of the drug to function normally. Additionally, chronic drug use results in less and less stimulation of the nucleus accumbens until eventually it produces no state of euphoria. This physical dependence is a combination of an increased tolerance to a drug and a physical need for the drug to function.

The method and regimen for blood level reduction described herein lead to gradual normalization of these changes over an extended period of time. The brain that had adapted to chronic chemical or drug use, now readapts to a chemical or drug-free state.

Withdrawal refers to the signs and symptoms that appear when an individual becomes physically dependent on a drug and drug use is suddenly discontinued or decreased in dosage. The appearance of withdrawal symptoms can be within a few hours or after several days of discontinuation. The time depends on the drug's elimination half-life. The discontinuation of drug use may produce a state of dysphoria, because the neurotransmitter levels within neural regions such as nucleus accumbens declines below normal levels. These subnormal levels may be characterized by depression, anxiety, and craving. Other common signs of withdrawal are increased heart rate and/or blood pressure, tremors, nausea, hallucinations, body aches, and excessive sweating, diarrhea, night terrors, restless leg syndrome, vomiting, dehydration, formications (crawling skin), as well as vivid or disturbing dreams of drug use. Some of the withdrawal symptoms themselves require hospitalization, such as hallucinations and seizures. Other possible serious risks include an increased danger to self and/or others.

The preferred embodiment of the present invention incorporates the use of a long term, controlled drug tapering regimen coupled with blood titration to determine blood levels of the drug substance in order to achieve the cessation of chemical or drug use. Unlike prior art approaches to treatment, the present invention achieves cessation of chemical or drug use by using a regimen that very gradually lowers blood levels for an extended period of time. A key aspect of the method and regimen of the present invention requires that the decrease in the lowest blood level from the previous lowest blood level of the chemical or drug substance cannot be more than five percent (5%).

This specific multidose strategy is also useful to inhibit withdrawal symptoms associated with abrupt cessation medications as noted in Section 2.

Development of the Variable Multidose Treatment Protocol to Reduce Physical Symptoms of Withdrawal After several years of clinical experience in the use of buprenorphine, it became clear that a single dose in mg of buprenorphine given over a short period of time would not lead to a drug-free status. Buprenorphine taken sublingually has a mean half-life of 12-37 hrs. If the dose is reduced rapidly, the patient reacts with both physical and emotional symptoms of withdrawal. By reducing the dose slowly, the patients experience a period where there is little or no decline in biologically available narcotic and thus feel more secure as they are not experiencing even minor withdrawal symptoms.

Accordingly, the drug rehabilitation protocol was altered to resemble the current protocol that will provide gradual reduced doses and blood levels, replacing the use of higher fixed doses.

Commercially available buprenorphine (Suboxone® & Subutex®) is available in strengths of 8.0 mg as well as 2.0 mg. However, that these medications would not suffice for a successful program, because the 2.0 mg dose was too large and too steep cut-off. A 2.0 mg dose reduction of buprenorphine caused significant withdrawal symptoms in an experienced or chronic user of narcotic type medications. As a result, reduction in dosage was be tapered below 1.0 mg as well as using two doses of buprenorphine daily for those patients who had very heavy daily narcotic use patterns (i.e. over 240.0 mg of OxyContin® daily).

During inception of development of multidose treatment that led to the current invention, and using the then current state of art, buprenorphine troches for the treatment (not maintenance) of opiate dependence was used on a patient that was a 21 years old male who was using I.V. 5-8 bags of heroin daily. He was started on 3 mg of buprenorphine and remained on this dose for three days. After a two day period without opiates, an attempt was made to administer the opiate blocker naltrexone which was intended to assure that a person is indeed drug free and remained so. However, this treatment did not succeed as severe withdrawal symptoms precipitated by this treatment resulted in his to return to drug use.

Many alterations in treatment protocols to prevent withdrawal were made. The alterations included a greater variety of doses ranging from 8.0 to 4.0 mg administered in a deceasing amount over time. At first the dose strengths varied from 8.0 mg administered once daily with a daily reduction of 2.0 mg until to 4.0 mg, and then to 2.0 mg. However during the earliest use of buprenorphine, it was understood that to go from administering 3.0 mg or even 2.0 mg to sobriety was too steep a cut-off point (i.e. patient would experience challenging withdrawal symptoms) and that fixed doses do not serve the patients well.

A 6.0 mg dose was then added to the protocol. This lengthened the withdrawal period from three days to seven. This change was occasioned by the observation that the drop from 8.0 mg to 4.0 mg was all too frequently accompanied by a significant return of withdrawal symptoms and, at times, a return to use.

Despite these alterations in the treatment protocol the results were still not what were expected. The observation was made that a cut-off of 2.0 mg would cause a return of withdrawal symptoms within 24 hrs and thus the likelihood of a return to drug use before naltrexone could be started. The data indicated that the downward transition or incremental decrease needed to be smoother. As a result, a 1.0 mg lozenges were administered A fractional buprenorphine dose was administered to reduce the severity of withdrawal symptoms. This strategy was in response to ongoing withdrawal symptoms following the "conclusion" of withdrawal or a "final" 3.0 mg dose of buprenorphine. To mitigate the withdrawal symptoms, a dose of 1.5 mg of buprenorphine was given to the patient. This particular treatment was unsuccessful as the ongoing withdrawal symptoms were too difficult for the patient who relapsed as a result.

Stepwise increments were amended to proceed in the sub 1.0 mg dose range. The taper at this time was 1.0 mg, 0.75 mg, 0.5 mg, to 0.25 mg then a four day period of blank troches followed by an upward taper of troches with naltrexone going from 0.5 mg of naltrexone to 10.0 mg of naltrexone. With serial doses of 0.25 mg of buprenorphine many patients continued to report perceptible and, in some cases, intolerable withdrawal symptoms.

As a result of the ongoing objective patient observations and patient's subjective complaints of withdrawal symptoms, a 0.1 mg dose was introduced. Additionally, a dose of 1.5 mg as well as a dose of 0.75 mg was added to the dose progression series. Although withdrawal complaints were limited, they were still present, and generally in the late phases of treatment. The data indicated that in order to reduce the complaints of withdrawal symptoms, the dose increments had to be further reduced in the sub 2.0 mg taper range. A strategy of 0.1 mg decreases in dose was implemented when the patients reached the 4.0 mg dose range (i.e., 2.0 mg twice a day) and 0.01 mg deceases in the below 1.0 mg range. The effect of this change also to extended the withdrawal period to about six to eight weeks from four weeks. The extended treatment time, allowed for concentrating the treatment on the psychological side of the dependency after the physical dependency subsided. This extension of service allowed for greater focus on the emergence of cravings as the patients approached the 2.0 mg barrier.

To further reduce the physical and psychological symptoms of withdrawal, the rate of taper or stepwise decrease in buprenorphine dose was reduced to 1.0 mg every other day and doses were given twice a day. Although successful for the most part in eliminating withdrawal symptoms, there continued to be a group of patients who were large users of longer acting narcotics such as Methadone and OxyContin® that found that they continued to have significant withdrawal symptoms. An induction phase of treatment is expanded from 3-5 days to 5-10 days before the withdrawal process is started. In an effort to eliminate the last vestiges of withdrawal symptoms, the taper was altered to reduce the dose to 5.0 mg every other day. Additionally, the number of sub 0.1 mg doses administered was increased resulting in a transition of almost 100% of our patients safely and in a symptomless manner from the opiate buprenorphine to the blocker naltrexone. The change further lengthened the treatment course from two months to three or more months. The length of treatment was dependent upon the daily dose of narcotics taken prior to entering treatment.

As a result, all of the treatments ended when an individual was successfully started on naltrexone, i.e., the individual was entirely off of narcotics. The protocol no longer stopped when buprenorphine content of the lozenges was discontinued. Instead, the patients returned daily and were given 'blank' lozenges. After a sufficient period to allow for a total washout of residual buprenorphine, the patients were transitioned to naltrexone 0.5 mg in lozenge form. This concentration then was gradually increased to 10.0 mg. When a patient reached 10.0 mg naltrexone in lozenge form, they were moved to naltrexone PO.

The methods described herein have been successful in individuals who were using massive amounts of pain killer type narcotics, such as doses of Fentanyl as Actiq in excess of 1200 mcgm #10 daily, as well as Methadone and illegal forms of opiates (Heroin 4+ gm IV daily). Patients to be treated include those with the following exemplary drug use profiles: Percocet® 500/10 mg, 5-30 tabs per day; Vicodin® 500/10 mg, 5-30 tabs per day; OxyContin® 10-80 mg, 1-25 tabs per day; Methadone 10-400 mg per day; MSContin® 100-400 mg per day; Fentanyl 75 1200 mcgm per day; Ultram® 50-100 mg 10-50 tabs per day; Diluadid® 4-76 mg per day; Demerol® 50-1500 mg per day; Heroin intranasally or intravenously 1 "bag" to 4 g per day; and Suboxone® 2-32 mg per day.

Since naltrexone is administered following the cessation of narcotic, there can be no residual narcotic in a patient's system, otherwise the naltrexone will push the patient into withdrawal. Therefore, the patient must wait about a week before to start naltrexone, even with extremely low doses, doses that may be considered to be homeopathic but are high enough to cause withdrawal symptoms if the narcotic is not fully washed out. As necessitated by the recognition that naltrexone, even administered at 12.5 mg, causes a return of withdrawal symptoms for up to five days after the end of buprenorphine treatment. The patient has to wait at least five days, remaining opiate free, before naltrexone could start.

Psycholoclical Withdrawal

Another change in the protocol dealt with the growing awareness of the psychology of opiate dependence, or the psychological withdrawal symptoms. Initially, all patients were informed daily of the dose that they were to receive in the office and the proposed dose schedule for their complete detoxification. This clearly caused distress with the patients who would become panicky or anxious upon learning that they would receive a smaller dose today than yesterday and that their treatment would likely end in four days time. The patients were exhibiting the psychological withdrawal symptoms associated with reducing the amount of opioid in their body.

Understanding psychological withdrawal symptoms, and seeing how it complicated the withdrawal process, the protocol was changed to: a) make all of the lozenges look and taste the same and b) absence of discussions regarding dose with patients as it lead to unnecessary anxiety. Instead, the discussion is focused on withdrawal symptoms and craving type symptoms. A craving is a dysphoric affective state that occurs in the process of withdrawal from a drug of dependence in the absence of NVD but may include physical symptoms of pain, malaise, insomnia, headache, anergia, anorexia, or vivid and disturbing dreams of drug use.

Further observations indicated that to end the treatment with a buprenorphine troche and then ask the patient to wait five to seven days before starting on naltrexone would likely lead to relapse. Therefore, naltrexone was compounded into fractional doses starting at 1.0 mg. By so doing, the time with no medication is shortened and the risk of any withdrawal symptoms is reduced by creating the blocking of opiate residue by naltrexone.

Rationale for Inhibition of Withdrawal Symptoms Associated with Cessation of Non-Opiates Most medications that have the potential for dependence are dosed so that they will be effective, i.e., they will resolve the target symptom be it pain, anxiety, seizures, depression etc. In contrast, the target symptom of the multidose approach is the withdrawal symptom(s); a therapeutic dose is one that does not cause withdrawal symptoms. Any medication that causes withdrawal symptoms upon abrupt cessation, when withdrawn slowly according to the multidosing schedule confers clinical benefit by reducing or eliminating physiological and/or psychological withdrawal symptoms.

Certain families of medications such as the benzodiazepines (Librium®, Valium®, Xanax®, Klonopin®, Ativan®, etc) have well known pathways that lead to their withdrawal states. Benzodiazepines that are abruptly stopped cause severe seizures as well as panic attacks. In addition, over time some individuals develop a psychological dependence on this type of medication as well as a physical one. For these individuals, a micro dose approach to cessation is the most clinically sound way to get a person off the drug. This approach especially applicable for those subjects, who have become dependent on this class of medication and who also have a concomitant alcohol dependence since the benzodiazepines and alcohol are seen as similar by the body.

Abrupt cessation of a benzodiazepine in an active drinker can cause that person to increase their alcohol consumption. For example, the effects of Xanax® withdrawal (as an example) are described below. What has become clinically apparent with Xanax® which appears to be somewhat different than the other benzodiazepines is that the patient's ability to self-detox (longer acting benzodiazepines such as Klonopin®/Valium®) or be able to be gradually tapered off of the medication is markedly more difficult. Thus once the physiologic dependence has occurred with Xanax®, the ability of the patient to discontinue use successfully on their own is quite low, and medical assistance becomes of significant necessity in the majority of cases. The withdrawal syndrome from Xanax® and other benzodiazepines are quite similar, with the exception that Xanax® has a much higher incidence of panic attack and a bereavement type of emotional lability that is singularly more severe. Since the symptoms are almost all internal, with a few physical or objective manifestations, the diagnosis of it can be very difficult. Patients have a difficult time verbally describing what is occurring, and much of the descriptions often take on a quality or character reminiscent of the emotional or psychiatric problem for which they originally began taking Xanax®, rather than a withdrawal symptom.

The withdrawal syndrome is diagnosed based on the following description of symptoms. In the early stage of withdrawal, there is a presentation of a sense of anxiety and apprehension associated with increasing subjective sense of tremor and mild bifrontal headache. This rapidly progresses to feelings of panic-like anxiety with tachycardia and palpitations, as well as a rapidly progressing feeling of de-realization, which is an altered sense of reality. Symptoms may also be associated with marked startle response and a general amplification of most sensory input. As the withdrawal syndrome progresses, there is a marked disturbance of proprioception, with difficulty in ambulation relative to feeling "dizzy" and "unsteady," needing to use reference and physical objects to steady oneself. With the proprioceptive problem increasing in severity simple acts such as swallowing, signing one's name, talking or even buttoning a shirt can become extremely difficult. many patients at this stage describe hot/cold sensations and generalized myalgia. There is also a progression of extreme emotional lability with sudden outbursts of crying or near panic levels of anxiety and fearfulness which will have sudden onset without clear connection to external events. Associated with this are frequent hypochodriacal fears of morbid consequence from the sensations they are feeling, such as fear of heart attack or stroke. Patients experience a type of emotional dysphoria which is very difficult for them to verbalize, but which come very close by cumulative description to a bereavement type of feeling that is very painful emotionally. Additionally, the amplification of almost all sensory information coming into the brain, other than that of taste, can produce many bizarre misinterpretation of sensory stimulation ranging from feeling one's teeth rotating in their sockets to parts of their bodies disassociating or "falling off".

As the withdrawal symptoms progress, illusionary and hallucinatory phenomena, predominately of a visual nature, begin to manifest themselves, initially with patterns and geometric shapes, and then into full-formed complex visual hallucinations. These symptoms also often become associated with delusions of bodily dysfunction or discorporation. It is frequent and common for the patient to conclude that he is having a nervous breakdown, or "going crazy" as an attempt to try to understand the process at hand, not understanding it as withdrawal phenomena. With further progression, disorientation to person and place occurs with full delirium, and eventually withdrawal will finalize with tonic-clonic major motor seizure activity, generally singular in nature, although several cases of status have been reported. The last triad of symptoms, hallucinosis, delirium and seizure, are classified as major symptoms of Xanax® withdrawal and other symptoms of drugs in this category. The withdrawal syndrome can take from months, e.g., 2-6 months, up to two years to fully resolve.

Another class of medication that is favorably withdrawn using the multidose regimen of the present invention is SSRI antidepressants, e.g., Paxil® and Zoloft®, as well as the non SSRI antidepressant Wellbutrin®. The methods are useful to safely and effectively reduce and then cease dependence on antidepressants such as those that inhibit neuronal uptake of serotonin, norepinephrine, and/or dopamine. The listed withdrawal symptoms for Paxil® are noted in the below chart and are representative of other SSRI type antidepressants. Complaints of insomnia and "body shock" are terrifying to a person wishing to get off of this medication but finding that they subject to highly unpleasant and disruptive consequences of sudden cessation such as: intense insomnia; extraordinarily vivid dreams; extreme confusion during waking hours; intense fear of losing sanity; steady feeling of existing outside of reality (depersonalization at times); memory and concentration problems; panic attacks; severe mood swings (heightened irritability/anger); suicidal thoughts; dizziness/vertigo; feeling of shocks (similar to mild electric one, running the length of your body); unsteady gait; slurred speech; headaches; profuse sweating, e.g., at night; muscle cramps; blurred vision; breaking out in tears; hypersensitivity to motion, sounds, smells; decreased appetite; nausea; abdominal cramping, diarrhea; loss of appetite; and/or chills/hot flashes.

Effexor® is another antidepressant with a withdrawal syndrome that is reduced or eliminated using a tapering multidose strategy. Prior to the invention, individuals seeking to cease medication struggled for years, e.g., two years. The schedule involved months skipping one day in between dose, nine months later two days in between, and as of three months ago, 3 days in between, followed by 4 days in between. Withdrawal symptoms included a sensation of buzzing (electrical impulses) upon eye or head movement, nausea, difficulty concentrating, forgetfulness, numbness in feet, twitching in the leg, disruptive sleep, night sweats, blurred vision, hallucinations, and difficulty with daily activities including work and driving. Tapered multidosing as described herein obviates the need to take off a week of work and allows the individual being treated to function without marked distress. Often such symptoms are rarely or not reported to physicians, and physicians currently have no strategy for dealing with the problem. Tapered multidosing gives the clinician the ability to rapidly and safely get their patients off of medications that pose a risk of substantial discomfort if they are not discontinued at a slow, steady and gradual pace. The strategy is also applicable to other antidepressants, e.g., the monoamine oxidase (MAO) inhibitor class of drugs such as Nardil®, Parnate®, and Marplan®, which may be associated with seizures if withdrawn rapidly.

Anti-seizure medication also poses a withdrawal risk, e.g., seizures, if abruptly terminated. However, tapered multidose reduction schedules for such drugs, e.g., barbiturates such as phenobarbitols, Dilantin®, Depacote®, reduce or eliminate the risk of adverse effects of cessation of the drug.

EXAMPLE 1

This patient began treatment with being administered a dosage of 6.0 mg of buprenorphine daily, via four lozenges. From there, the dosage of buprenorphine decreased daily by 0.5 mg, until the dosage was 2.0 mg. From there the patient's dosage was decreased 0.2 mg a day until the dosage was 1.0 mg. At that point, the dosage was reduced by 0.1 mg a day and the dosage of 0.2 mg was given for two days. When the patient reached a dosage of 0.1 mg, the dosage was then dropped to 0.05 mg, however, due to the patient suffering from withdrawal symptoms, the dosage was increased to 0.1 mg, which was administered for three days. At which point the dosage was again decreased to 0.05 mg a day for two days. The dosage was then decreased to 0.03 mg, then to 0.01 mg of the last day of treatment with buprenorphine.

The patient was then given a 1.0 mg dosage of Quinine. On the last day the patient was given a 100 mg dosage of Seroquel®. A summary of the dosage can be seen in Table 1 below:

TABLE 1

| Prescription No. | Medication | Dosage (mg) | No. of Lozenges | Directions/Frequency |
|---|---|---|---|---|
| 8412 | Buprenorphine Troche | 6.00 | 4 | Take 1 Troche sublingually Twice daily |
| 8413 | Buprenorphine Troche | 5.50 | 4 | Take 1 Troche sublingually Twice daily |
| 8414 | Buprenorphine Troche | 5.00 | 4 | Take 1 Troche sublingually Twice daily |
| 8415 | Buprenorphine Troche | 4.50 | 4 | Take 1 Troche sublingually Twice daily |
| 8416 | Buprenorphine Troche | 4.00 | 4 | Take 1 Troche sublingually Twice daily |
| 8417 | Buprenorphine Troche | 3.50 | 4 | Take 1 Troche sublingually Twice daily |
| 8418 | Buprenorphine Troche | 3.00 | 4 | Take 1 Troche sublingually Twice daily |
| 8419 | Buprenorphine Troche | 2.00 | 4 | Take 1 Troche sublingually Twice daily |
| 8420 | Buprenorphine Troche | 1.80 | 4 | Take 1 Troche sublingually Twice daily |
| 8421 | Buprenorphine Troche | 1.60 | 4 | Take 1 Troche sublingually Twice daily |
| 8422 | Buprenorphine Troche | 1.40 | 4 | Take 1 Troche sublingually Twice daily |
| 8423 | Buprenorphine Troche | 1.20 | 4 | Take 1 Troche sublingually Twice daily |
| 8424 | Buprenorphine Troche | 1.00 | 4 | Take 1 Troche sublingually Twice daily |
| 8425 | Buprenorphine Troche | 0.90 | 4 | Take 1 Troche sublingually Twice daily |
| 8426 | Buprenorphine Troche | 0.80 | 4 | Take 1 Troche sublingually Twice daily |
| 8427 | Buprenorphine Troche | 0.70 | 4 | Take 1 Troche sublingually Twice daily |
| 8428 | Buprenorphine Troche | 0.60 | 4 | Take 1 Troche sublingually Twice daily |
| 8429 | Buprenorphine Troche | 0.50 | 4 | Take 1 Troche sublingually Twice daily |
| 8430 | Buprenorphine Troche | 0.40 | 4 | Take 1 Troche sublingually Twice daily |
| 8431 | Buprenorphine Troche | 0.30 | 4 | Take 1 Troche sublingually Twice daily |
| 8432 | Buprenorphine Troche | 0.20 | 4 | Take 1 Troche sublingually Twice daily |
| 8433 | Buprenorphine Troche | 0.20 | 4 | Take 1 Troche sublingually Twice daily |
| 8434 | Buprenorphine Troche | 0.10 | 4 | Take 1 Troche sublingually Twice daily |
| 8435 | Buprenorphine Troche | 0.05 | 4 | Take 1 Troche sublingually Twice daily |
| 8729 | Buprenorphine Troche | 0.10 | 4 | Take 1 Troche sublingually Twice daily |
| 8730 | Buprenorphine Troche | 0.10 | 8 | Take 1 Troche sublingually Twice daily |
| 8731 | Buprenorphine Troche | 0.10 | 8 | Take 1 Troche sublingually Twice daily |
| 8732 | Buprenorphine Troche | 0.05 | 8 | Take 1 Troche sublingually Twice daily |
| 8854 | Buprenorphine Troche | 0.05 | 8 | Take 1 Troche sublingually Twice daily |
| 8855 | Buprenorphine Troche | 0.03 | 8 | Take 1 Troche sublingually Twice daily |

TABLE 1-continued

| Prescription No. | Medication | Dosage (mg) | No. of Lozenges | Directions/Frequency |
|---|---|---|---|---|
| 8856 | Buprenorphine Troche | 0.01 | 8 | Take 1 Troche sublingually Twice daily |
| 8438 | Naltrexone Troche | 0.50 | 3 | Take 1 Troche sublingually Twice daily |
| 8436 | Quinine Troche | 1.00 | 4 | Take 1 Troche sublingually Twice daily |
| 8437 | Quinine Troche | 1.00 | 4 | Take 1 Troche sublingually Twice daily |
| tel | Seroquel | 100.00 | 120 | Tab ii-iv po qHS prn onsomnia |

EXAMPLE 2

This patient began treatment with being administered a dosage of 6.0 mg of buprenorphine daily, via nine lozenges. From there the dosage of buprenorphine decreased daily by 0.25 mg, until the dosage was 2.0 mg. From there, the patient's dosage was decreased 0.2 mg a day until the dosage was 1.0 mg. At that point, the dosage was reduced by 0.1 mg a day. When the patient reached a dosage of 0.1 mg, the dosage was then dropped to 0.05 mg, the dosage was then 0.03 mg, and finally 0.01 mg on the final day of treatment with of buprenorphine.

The patient was then given a 1.0 mg dosage of Quinine for two days. On the last day the patient was given a 0.5 mg dosage of naltrexone. A summary of the dosage can be seen in Table 2 below:

TABLE 2

| Prescription No. | Medication | Dosage (mg) | No. of Lozenges | Directions/Frequency |
|---|---|---|---|---|
| 9013 | Buprenorphine Troche | 6.00 | 9 | Take 1 Troche sublingually Four Times Daily |
| 9014 | Buprenorphine Troche | 5.75 | 9 | Take 1 Troche sublingually Four Times Daily |
| 9015 | Buprenorphine Troche | 5.50 | 9 | Take 1 Troche sublingually Four Times Daily |
| 9016 | Buprenorphine Troche | 5.25 | 9 | Take 1 Troche sublingually Four Times Daily |
| 9017 | Buprenorphine Troche | 5.00 | 9 | Take 1 Troche sublingually Four Times Daily |
| 9018 | Buprenorphine Troche | 4.75 | 9 | Take 1 Troche sublingually Four Times Daily |
| 9019 | Buprenorphine Troche | 4.50 | 9 | Take 1 Troche sublingually Four Times Daily |
| 9020 | Buprenorphine Troche | 4.25 | 9 | Take 1 Troche sublingually Four Times Daily |
| 9021 | Buprenorphine Troche | 4.00 | 9 | Take 1 Troche sublingually Four Times Daily |
| 9022 | Buprenorphine Troche | 3.75 | 9 | Take 1 Troche sublingually Four Times Daily |
| 9023 | Buprenorphine Troche | 3.50 | 9 | Take 1 Troche sublingually Four Times Daily |
| 9024 | Buprenorphine Troche | 3.25 | 9 | Take 1 Troche sublingually Four Times Daily |
| 9025 | Buprenorphine Troche | 3.00 | 9 | Take 1 Troche sublingually Four Times Daily |
| 9026 | Buprenorphine Troche | 2.75 | 9 | Take 1 Troche sublingually Four Times Daily |
| 9027 | Buprenorphine Troche | 2.50 | 9 | Take 1 Troche sublingually Four Times Daily |
| 9028 | Buprenorphine Troche | 2.25 | 9 | Take 1 Troche sublingually Four Times Daily |
| 9029 | Buprenorphine Troche | 2.00 | 9 | Take 1 Troche sublingually Four Times Daily |
| 9053 | Buprenorphine Troche | 1.80 | 9 | Take 1 Troche sublingually Four Times Daily |
| 9054 | Buprenorphine Troche | 1.60 | 9 | Take 1 Troche sublingually Four Times Daily |
| 9055 | Buprenorphine Troche | 1.40 | 9 | Take 1 Troche sublingually Four Times Daily |
| 9056 | Buprenorphine Troche | 1.20 | 9 | Take 1 Troche sublingually Four Times Daily |
| 9057 | Buprenorphine Troche | 1.00 | 9 | Take 1 Troche sublingually Four Times Daily |
| 9058 | Buprenorphine Troche | 0.90 | 9 | Take 1 Troche sublingually Four Times Daily |
| 9059 | Buprenorphine Troche | 0.80 | 9 | Take 1 Troche sublingually Four Times Daily |
| 9060 | Buprenorphine Troche | 0.70 | 9 | Take 1 Troche sublingually Four Times Daily |
| 9061 | Buprenorphine Troche | 0.60 | 9 | Take 1 Troche sublingually Four Times Daily |
| 9062 | Buprenorphine Troche | 0.50 | 9 | Take 1 Troche sublingually Four Times Daily |
| 9063 | Buprenorphine Troche | 0.40 | 9 | Take 1 Troche sublingually Four Times Daily |
| 9064 | Buprenorphine Troche | 0.30 | 9 | Take 1 Troche sublingually Four Times Daily |
| 9065 | Buprenorphine Troche | 0.20 | 9 | Take 1 Troche sublingually Four Times Daily |
| 9066 | Buprenorphine Troche | 0.10 | 9 | Take 1 Troche sublingually Four Times Daily |
| 9067 | Buprenorphine Troche | 0.05 | 9 | Take 1 Troche sublingually Four Times Daily |
| 9068 | Buprenorphine Troche | 0.03 | 9 | Take 1 Troche sublingually Four Times Daily |
| 9069 | Buprenorphine Troche | 0.01 | 9 | Take 1 Troche sublingually Four Times Daily |
| 9070 | Quinine Troche | 1.00 | 9 | Take 1 Troche sublingually Four Times Daily |
| 9071 | Quinine Troche | 1.00 | 9 | Take 1 Troche sublingually Four Times Daily |
| 9072 | Naltrexone Troche | 0.50 | 4 | Take 1 Troche sublingually Once Daily |

EXAMPLE 3

This patient began treatment with being administered a dosage of 7.5 mg of buprenorphine daily, via four lozenges. From there the dosage of buprenorphine decreased daily by 0.5 mg, until the dosage was 2.0 mg. From there, the patient's dosage was decreased 0.2 mg a day until the dosage was 1.0 mg. At that point, the dosage was reduced by 0.1 mg a day. When the patient reached a dosage of 0.1 mg, the dosage was then dropped by 0.02 mg each day until finally the dosage was mg on the final day of treatment with of buprenorphine.

The patient was then given a 1.0 mg dosage of Quinine for four days. On the last day the patient was given a 0.5 mg dosage of naltrexone. A summary of the dosage can be seen in Table 3 below:

TABLE 3

| Prescription No. | Medication | Dosage (mg) | No. of Lozenges | Directions/Frequency |
|---|---|---|---|---|
| 8892 | Buprenorphine Troche | 7.50 | 4 | Take 1 Troche sublingually Twice Daily |
| 8893 | Buprenorphine Troche | 7.00 | 4 | Take 1 Troche sublingually Twice Daily |
| 8894 | Buprenorphine Troche | 6.50 | 4 | Take 1 Troche sublingually Twice Daily |
| 8895 | Buprenorphine Troche | 6.00 | 4 | Take 1 Troche sublingually Twice Daily |
| 8896 | Buprenorphine Troche | 5.50 | 4 | Take 1 Troche sublingually Twice Daily |
| 8897 | Buprenorphine Troche | 5.00 | 4 | Take 1 Troche sublingually Twice Daily |
| 8898 | Buprenorphine Troche | 4.50 | 4 | Take 1 Troche sublingually Twice Daily |
| 8899 | Buprenorphine Troche | 4.00 | 4 | Take 1 Troche sublingually Twice Daily |
| 8900 | Buprenorphine Troche | 3.50 | 4 | Take 1 Troche sublingually Twice Daily |
| 8901 | Buprenorphine Troche | 3.00 | 4 | Take 1 Troche sublingually Twice Daily |
| 8902 | Buprenorphine Troche | 2.50 | 4 | Take 1 Troche sublingually Twice Daily |
| 8903 | Buprenorphine Troche | 2.00 | 4 | Take 1 Troche sublingually Twice Daily |
| 8904 | Buprenorphine Troche | 1.80 | 4 | Take 1 Troche sublingually Twice Daily |
| 8905 | Buprenorphine Troche | 1.60 | 4 | Take 1 Troche sublingually Twice Daily |
| 8906 | Buprenorphine Troche | 1.40 | 4 | Take 1 Troche sublingually Twice Daily |
| 8907 | Buprenorphine Troche | 1.20 | 4 | Take 1 Troche sublingually Twice Daily |
| 8908 | Buprenorphine Troche | 1.00 | 4 | Take 1 Troche sublingually Twice Daily |
| 8909 | Buprenorphine Troche | 0.90 | 4 | Take 1 Troche sublingually Twice Daily |
| 8910 | Buprenorphine Troche | 0.80 | 4 | Take 1 Troche sublingually Twice Daily |
| 8911 | Buprenorphine Troche | 0.70 | 4 | Take 1 Troche sublingually Twice Daily |
| 8912 | Buprenorphine Troche | 0.60 | 4 | Take 1 Troche sublingually Twice Daily |
| 8913 | Buprenorphine Troche | 0.50 | 4 | Take 1 Troche sublingually Twice Daily |
| 8914 | Buprenorphine Troche | 0.40 | 4 | Take 1 Troche sublingually Twice Daily |
| 8915 | Buprenorphine Troche | 0.30 | 4 | Take 1 Troche sublingually Twice Daily |
| 8916 | Buprenorphine Troche | 0.20 | 4 | Take 1 Troche sublingually Twice Daily |
| 8917 | Buprenorphine Troche | 0.10 | 4 | Take 1 Troche sublingually Twice Daily |
| 8918 | Buprenorphine Troche | 0.08 | 4 | Take 1 Troche sublingually Twice Daily |
| 8919 | Buprenorphine Troche | 0.06 | 4 | Take 1 Troche sublingually Twice Daily |
| 8920 | Buprenorphine Troche | 0.05 | 4 | Take 1 Troche sublingually Twice Daily |
| 8921 | Buprenorphine Troche | 0.03 | 4 | Take 1 Troche sublingually Twice Daily |
| 8922 | Buprenorphine Troche | 0.01 | 4 | Take 1 Troche sublingually Twice Daily |
| 8923 | Quinine Troche | 1.00 | 4 | Take 1 Troche sublingually Twice Daily |
| 8924 | Quinine Troche | 1.00 | 4 | Take 1 Troche sublingually Twice Daily |
| 8925 | Quinine Troche | 1.00 | 4 | Take 1 Troche sublingually Twice Daily |
| 8926 | Quinine Troche | 1.00 | 4 | Take 1 Troche sublingually Twice Daily |
| 8927 | Naltrexone Troche | 0.50 | 4 | Take 1 Troche sublingually Once Daily |

EXAMPLE 4

This patient began treatment having buprenorphine being administered a dosage of 4.0 mg of buprenorphine. Typically, a patient is given two doses of medication, at the same amount of buprenorphine, daily spaced approximately 12 hours apart and each dose is given for about two days. From there the each new dosage of buprenorphine decreased overtime by 10%, until dosage 16, at which point, the patient's dosage was decreased 15% for three dosages. At that point, the dosage was reduced by 20% for each dosage over the course of two dosages. The next two dosages were reduced 25%. The dosages from dosage 23 to dosage 30 were reduced by another 30% per dosage. A summary of the dosage can be seen in Table 4 below:

TABLE 4

| Dosage No. | Buprenorphine (mg) | % Decrease |
|---|---|---|
| 1 | 4.00 | 10 |
| 2 | 3.60 | 10 |
| 3 | 3.24 | 10 |
| 4 | 2.92 | 10 |
| 5 | 2.62 | 10 |
| 6 | 2.36 | 10 |
| 7 | 2.13 | 10 |
| 8 | 1.91 | 10 |
| 9 | 1.72 | 10 |
| 10 | 1.55 | 10 |
| 11 | 1.39 | 10 |
| 12 | 1.26 | 10 |
| 13 | 1.13 | 10 |
| 14 | 1.02 | 10 |
| 15 | 0.92 | 10 |
| 16 | 0.82 | 15 |
| 17 | 0.70 | 15 |
| 18 | 0.60 | 15 |
| 19 | 0.51 | 20 |
| 20 | 0.40 | 20 |
| 21 | 0.32 | 25 |
| 22 | 0.24 | 25 |
| 23 | 0.18 | 30 |
| 24 | 0.13 | 30 |
| 25 | 0.09 | 30 |
| 26 | 0.06 | 30 |
| 27 | 0.04 | 30 |
| 28 | 0.03 | 30 |
| 29 | 0.02 | 30 |
| 30 | 0.01 | 30 |

EXAMPLE 5

This patient began treatment having buprenorphine being administered a dosage of 8.0 mg of buprenorphine, twice a day. Typically, a patient is given two doses of medication, at the same amount of buprenorphine, daily spaced approximately 12 hours apart and each dose is given for about two days. Each two-day period is defined as a dosing period. The decrease in the dosing amount per dosing period was 0.5 mg until 6 mg was reached and then each dosing amount per dosing period was decreased by 0.25 mg. At 4 mg, the dosing amount per period was decreased by 0.2 mg until 2 mg was reached and then each dosing amount per dosing period was decreased by 0.02 mg. At 0.08 mg, the dosing amount per period was then decreased by 0.01 mg until 0.0 mg was reached. The total days of the decreasing regimen was 71 days. A placebo was given for 4-5 days before naltrexone administration began. FIG. 1 shows a graphical representation of the rate of decline of the amount of buprenorphine administered and a summary of the dosage can be seen in Table 5 below:

TABLE 5

| Day | AM | PM | Total BN |
|---|---|---|---|
| 1 | 8 mg | 8 mg | 16 mg |
| 2 | 8 mg | 8 mg | 16 mg |
| 3 | 8 mg | 7.5 mg | 15.5 mg |
| 4 | 7.5 mg | 7.5 mg | 15 mg |
| 5 | 7.5 mg | 7 mg | 14.5 mg |
| 6 | 7 mg | 7 mg | 14 mg |
| 7 | 7 mg | 6.5 mg | 13.5 mg |
| 8 | 6.5 mg | 6.5 mg | 13 mg |
| 9 | 6.5 mg | 6 mg | 12.5 mg |
| 10 | 6 mg | 6 mg | 12 mg |
| 11 | 6 mg | 5.5 mg | 11.5 mg |
| 12 | 5.5 mg | 5.5 mg | 11 mg |
| 13 | 5.5 mg | 5 mg | 10.5 mg |
| 14 | 5 mg | 5 mg | 10 mg |
| 15 | 5 mg | 4.5 mg | 9.5 mg |
| 16 | 4.5 mg | 4.5 mg | 9 mg |
| 17 | 4.5 mg | 4 mg | 8.5 mg |
| 18 | 4 mg | 4 mg | 8 mg |
| 19 | 4 mg | 3.5 mg | 7.5 mg |
| 20 | 3.5 mg | 3.5 mg | 7 mg |
| 21 | 3.5 mg | 3 mg | 6.5 mg |
| 22 | 3 mg | 3 mg | 6 mg |
| 23 | 3 mg | 2.75 mg | 5.75 mg |
| 24 | 2.75 mg | 2.75 mg | 5.5 mg |
| 25 | 2.75 mg | 2.5 mg | 5.25 mg |
| 26 | 2.5 mg | 2.5 mg | 5 mg |
| 27 | 2.5 mg | 2.25 mg | 4.75 mg |
| 28 | 2.25 mg | 2.25 mg | 4.5 mg |
| 29 | 2.25 mg | 2 mg | 4.25 mg |
| 30 | 2 mg | 2 mg | 4 mg |
| 31 | 2 mg | 1.8 mg | 3.8 mg |
| 32 | 1.8 mg | 1.8 mg | 3.6 mg |
| 33 | 1.8 mg | 1.6 mg | 3.4 mg |
| 34 | 1.6 mg | 1.6 mg | 3.2 mg |
| 35 | 1.6 mg | 1.4 mg | 3 mg |
| 36 | 1.4 mg | 1.4 mg | 2.8 mg |
| 37 | 1.4 mg | 1.2 mg | 2.6 mg |
| 38 | 1.2 mg | 1.2 mg | 2.4 mg |
| 39 | 1.2 mg | 1.0 mg | 2.2 mg |
| 40 | 1.0 mg | 1.0 mg | 2 mg |
| 41 | 1.0 mg | 0.9 mg | 1.9 mg |
| 42 | 0.9 mg | 0.9 mg | 1.8 mg |
| 43 | 0.9 mg | 0.8 mg | 1.7 mg |
| 44 | 0.8 mg | 0.8 mg | 1.6 mg |
| 45 | 0.8 mg | 0.7 mg | 1.5 mg |
| 46 | 0.7 mg | 0.7 mg | 1.4 mg |
| 47 | 0.7 mg | 0.6 mg | 1.3 mg |
| 48 | 0.6 mg | 0.6 mg | 1.2 mg |
| 49 | 0.6 mg | 0.5 mg | 1.1 mg |
| 50 | 0.5 mg | 0.5 mg | 1.0 mg |
| 51 | 0.5 mg | 0.4 mg | 0.9 mg |
| 52 | 0.4 mg | 0.4 mg | 0.8 mg |
| 53 | 0.4 mg | 0.3 mg | 0.7 mg |
| 54 | 0.3 mg | 0.3 mg | 0.6 mg |
| 55 | 0.3 mg | 0.2 mg | 0.5 mg |
| 56 | 0.2 mg | 0.2 mg | 0.4 mg |
| 57 | 0.2 mg | 0.1 mg | 0.3 mg |
| 58 | 0.1 mg | 0.1 mg | 0.2 mg |
| 59 | 0.1 mg | 0.08 mg | 0.18 mg |
| 60 | 0.08 mg | 0.08 mg | 0.16 mg |
| 61 | 0.08 mg | 0.06 mg | 0.14 mg |
| 62 | 0.06 mg | 0.06 mg | 0.12 mg |
| 63 | 0.06 mg | 0.04 mg | 0.1 mg |
| 64 | 0.04 mg | 0.04 mg | 0.08 mg |
| 65 | 0.04 mg | 0.03 mg | 0.07 mg |
| 66 | 0.03 mg | 0.03 mg | 0.06 mg |
| 67 | 0.03 mg | 0.02 mg | 0.05 mg |
| 68 | 0.02 mg | 0.02 mg | 0.04 mg |
| 69 | 0.02 mg | 0.01 mg | 0.03 mg |
| 70 | 0.01 mg | 0.01 mg | 0.02 mg |
| 71 | 0.01 mg | 0 mg | 0.01 mg |
| Quinine | | | |
| 72 | 1 mg | | 0 mg |
| 73 | 1 mg | | 0 mg |
| 74 | 1 mg | | 0 mg |
| 75 | 1 mg | | 0 mg |

TABLE 5-continued

| Day | AM | PM | Total BN |
|---|---|---|---|
| | | Naltrexone | |
| 76 | 0.5 mg | | 0.5 mg |
| 77 | 0.5 mg | 0.5 mg | 1 mg |
| 78 | 1 mg | 1 mg | 2 mg |
| 79 | 2 mg | 2 mg | 4 mg |
| 80 | 5 mg | 5 mg | 10 mg |
| qd | | Vivitrol (naltrexone IM LA) or naltrexone 50 mg | |

Figure 2:
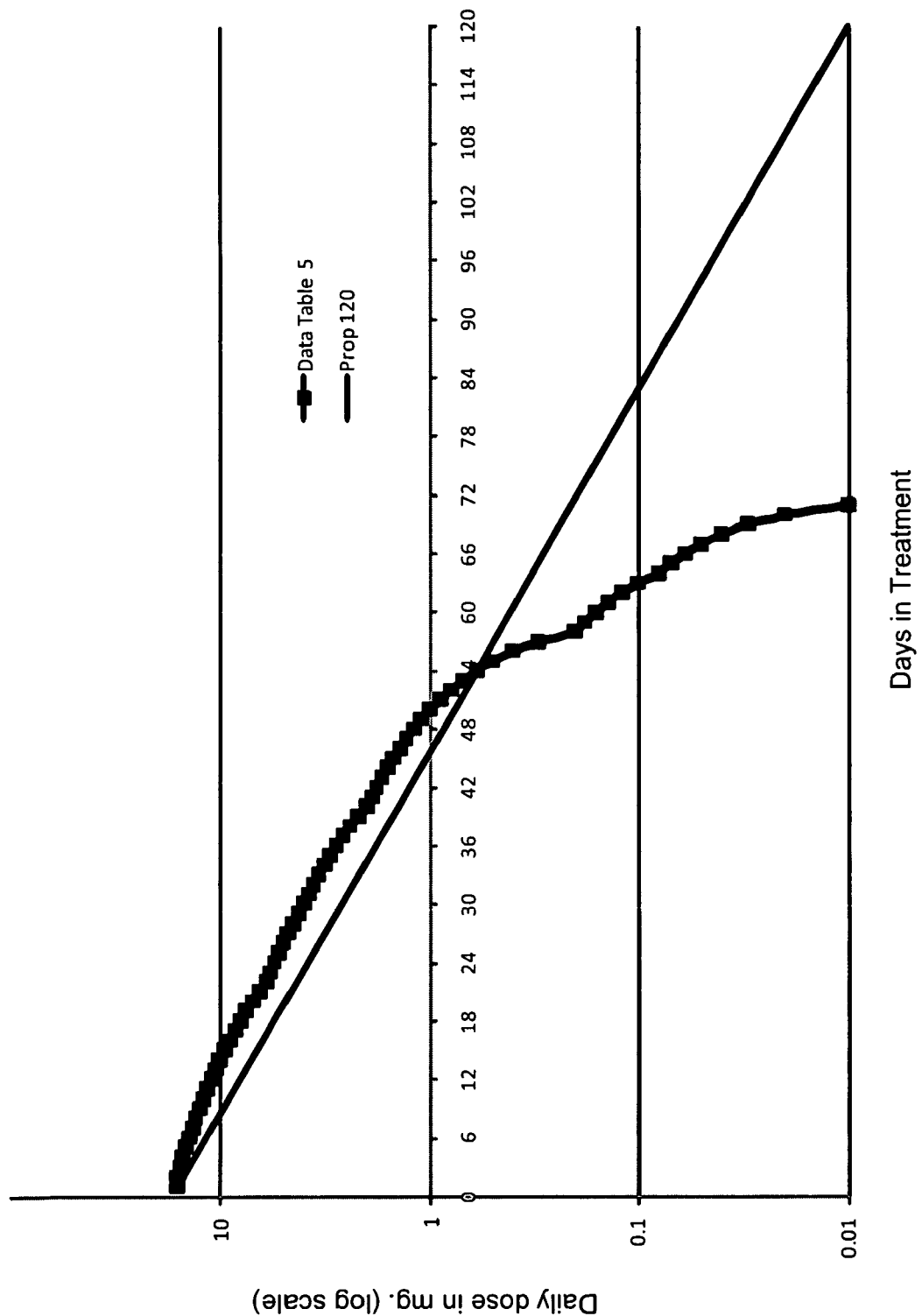
FIG. 2 is a graphic illustration of the dosage regimen data for example 5 plotted on semi log form.

It was further discovered that there were additional problems that appeared during the 71 day regimen as it relates to the concentration levels of the drug in the blood stream. These problems with dosing and withdrawal issues occurred around the fiftieth day of the regimen. Consequently, the data of Table 6 was then plotted on a semi log. FIG. 2 shows a graphical representation of the dosing regimen plotted as a log scale. It appears that the curve is closely linear over the first fifty days but then declines more rapidly. A review of the dosing data indicated that the decrease in dosing and the linearity of the log curve was closely tied to the relative difference of the dosing amount in a subsequent dosing period to the dosing amount in the previous dosing period. The problem was determined to be the lowest level of the drug substance present in the blood plasma before the next dosing amount in the next dosing period.

From data based on high success rates (90% or greater) in achieving freedom from physical dependence to opioids and related substances using specific gradually decreasing but measured doses, and projected blood levels based on the pharmacokinetic profile of the replacement narcotic buprenorphine hydrochloride that has an opioid agonist effect, it was concluded that blood level reductions of no greater than five percent (5%) per day from the previous day can lead to successful cessation of use. The data included the treatment of patients on agents that included buprenorphine, codeine, fentanyl, heroin (diacetylmorphine), hydrocodone, hydromorphone, methadone, morphine, oxycodone, proposyphene, tramadol, other opiates, and non-opiates such as pentazocine. The results indicated that the highest success rate in drug cessation was achieved beyond 90 days. The final results by treatment days using a replacement narcotic compound buprenorphine hydrochloride that achieved calculated blood levels of no greater than five percent (5%) reduction from the previous period are illustrated in Table 6

TABLE 6

| | Total | Successful | |
|---|---|---|---|
| 1-30 days | 75 | 38 | 50.7% |
| 31-60 days | 52 | 39 | 75.0% |
| 61-90 days | 21 | 19 | 90.5% |

Figure 3:
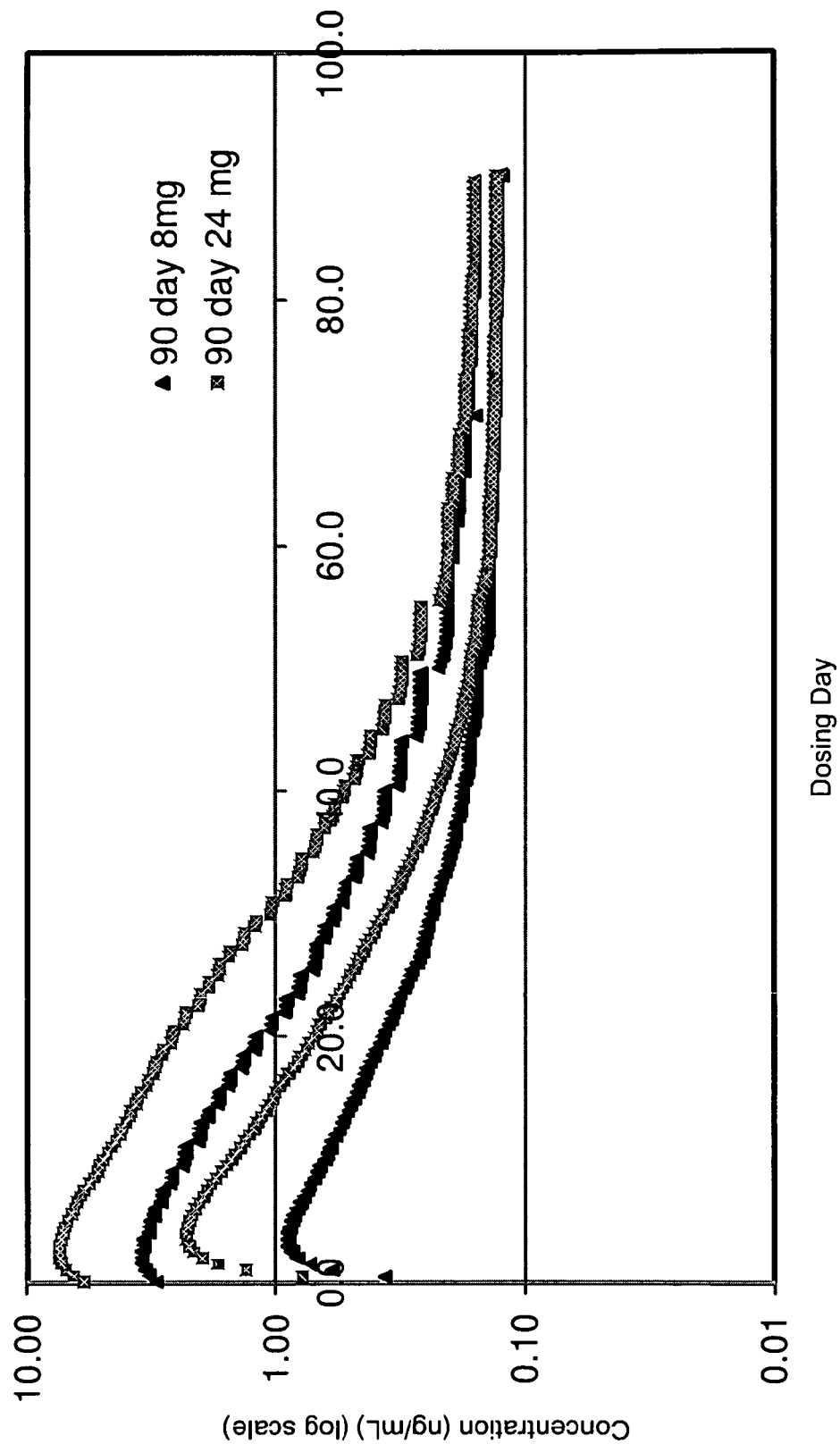
FIG. 3 is a graphic illustration of the dosage regimen data of the calculated peak and lowest concentration of buprenorphine hydrochloride in the blood represented by Table 7 and plotted in semi log form for a 90 day regimen.

To confirm these findings, numerical tabulations for multidosing involving buprenorphine for ninety (90) and one hundred twenty (120) days confirm the gradual blood level changes required for successful cessation. The original data contains data at different dosing levels of 8 mg, 12 mg, 16 mg, and 24 mg. Some of the data (the first 15 days of data of the 90 days) for the 8 mg and 24 mg is shown in Table 7 for the 90-day regimen while FIG. 3 shows a graphical illustration of all of the data showing the peak and lowest level concentrations for the 90-day regimen. Because peak concentration of a drug substance in the blood typically occurs about 1 hour after taking, blood concentration levels were calculated from empirical data 1 hour after a dose is administered and immediately before the next dose is administered to obtain peak concentration and lowest level concentration. The tapering is performed in a gradual decreasing format based on a log curve similar to the log curve of the actual data of the first 40-50 days of Table 5.

TABLE 7

| Dose Time (day) | Dose time(hr) | Multidose 90 days ng/mL 8 mg | Trough ng/mL | Slope | Change from prev | Multidose 90 days ng/mL 24 mg | Trough ng/mL | Slope | Change from prev |
|---|---|---|---|---|---|---|---|---|---|
| 0.0 | 0 | 0.00 | 0.00 | | | 0.00 | 0.00 | | |
| 0.0 | 1 | 2.98 | | | | 5.90 | | | |
| 0.5 | 12 | 0.36 | 0.36 | | | 0.79 | 0.79 | | |
| 0.5 | 13 | 3.20 | | | | 6.49 | | | |
| 1.0 | 24 | 0.59 | 0.59 | | | 1.32 | 1.32 | | |
| 1.0 | 25 | 3.32 | | | | 7.01 | | | |
| 1.5 | 36 | 0.72 | 0.72 | | | 1.71 | 1.71 | | |
| 1.5 | 37 | 3.45 | | | | 7.27 | | | |
| 2.0 | 48 | 0.82 | 0.82 | | | 1.97 | 1.97 | | |
| 2.0 | 49 | 3.41 | | | | 7.40 | | | |
| 2.5 | 60 | 0.86 | 0.86 | | | 2.13 | 2.13 | | |
| 2.5 | 61 | 3.45 | | | | 7.42 | | | |
| 3.0 | 72 | 0.89 | 0.89 | | | 2.23 | 2.23 | | |
| 3.0 | 73 | 3.36 | | | | 7.43 | | | |
| 3.5 | 84 | 0.89 | 0.89 | | | 2.28 | 2.28 | | |
| 3.5 | 85 | 3.36 | | | | 7.32 | | | |
| 4.0 | 96 | 0.89 | 0.89 | | | 2.28 | 2.28 | | |
| 4.0 | 97 | 3.21 | | | | 7.15 | | | |
| 4.5 | 108 | 0.87 | 0.87 | −0.040 | −2.2% | 2.26 | 2.26 | −0.040 | −0.9% |
| 4.5 | 109 | 3.19 | | | | 7.03 | | | |
| 5.0 | 120 | 0.86 | 0.86 | −0.020 | −1.1% | 2.22 | 2.22 | −0.080 | −1.8% |
| 5.0 | 121 | 3.18 | | | | 6.90 | | | |
| 5.5 | 132 | 0.84 | 0.84 | −0.040 | −2.3% | 2.17 | 2.17 | −0.100 | −2.3% |
| 5.5 | 133 | 3.06 | | | | 6.65 | | | |
| 6.0 | 144 | 0.81 | 0.81 | −0.060 | −3.6% | 2.11 | 2.11 | −0.120 | −2.8% |
| 6.0 | 145 | 3.03 | | | | 6.48 | | | |
| 6.5 | 156 | 0.79 | 0.79 | −0.040 | −2.5% | 2.04 | 2.04 | −0.140 | −3.3% |
| 6.5 | 157 | 2.87 | | | | 6.30 | | | |

TABLE 7-continued

| Dose Time (day) | Dose time(hr) | Multidose 90 days ng/mL 8 mg | Trough ng/mL | Slope | Change from prev | Multidose 90 days ng/mL 24 mg | Trough ng/mL | Slope | Change from prev |
|---|---|---|---|---|---|---|---|---|---|
| 7.0 | 168 | 0.76 | 0.76 | −0.060 | −3.8% | 1.96 | 1.96 | −0.160 | −3.9% |
| 7.0 | 169 | 2.84 | | | | 6.12 | | | |
| 7.5 | 180 | 0.74 | 0.74 | −0.040 | −2.6% | 1.89 | 1.89 | −0.140 | −3.6% |
| 7.5 | 181 | 2.81 | | | | 5.93 | | | |
| 8.0 | 192 | 0.72 | 0.72 | −0.040 | −2.7% | 1.82 | 1.82 | −0.140 | −3.7% |
| 8.0 | 193 | 2.62 | | | | 5.61 | | | |
| 8.5 | 204 | 0.69 | 0.69 | −0.060 | −4.2% | 1.73 | 1.73 | −0.180 | −4.9% |
| 8.5 | 205 | 2.59 | | | | 5.40 | | | |
| 9.0 | 216 | 0.68 | 0.68 | −0.020 | −1.4% | 1.65 | 1.65 | −0.160 | −4.6% |
| 9.0 | 217 | 2.57 | | | | 5.19 | | | |
| 9.5 | 228 | 0.66 | 0.66 | −0.040 | −2.9% | 1.57 | 1.57 | −0.160 | −4.8% |
| 9.5 | 229 | 2.34 | | | | 5.11 | | | |
| 10.0 | 240 | 0.63 | 0.63 | −0.060 | −4.5% | 1.52 | 1.52 | −0.100 | −3.2% |
| 10.0 | 241 | 2.31 | | | | 4.95 | | | |
| 10.5 | 252 | 0.62 | 0.62 | −0.020 | −1.6% | 1.46 | 1.46 | −0.120 | −3.9% |
| 10.5 | 253 | 2.29 | | | | 4.76 | | | |
| 11.0 | 264 | 0.60 | 0.60 | −0.040 | −3.2% | 1.40 | 1.40 | −0.120 | −4.1% |
| 11.0 | 265 | 2.28 | | | | 4.55 | | | |
| 11.5 | 276 | 0.60 | 0.60 | 0.000 | −0.0% | 1.34 | 1.34 | −0.120 | −4.3% |
| 11.5 | 277 | 2.05 | | | | 4.40 | | | |
| 12.0 | 288 | 0.57 | 0.57 | −0.060 | −5.0% | 1.29 | 1.29 | −0.100 | −3.7% |
| 12.0 | 289 | 2.02 | | | | 4.22 | | | |
| 12.5 | 300 | 0.55 | 0.55 | −0.040 | −3.5% | 1.23 | 1.23 | −0.120 | −4.7% |
| 12.5 | 301 | 2.00 | | | | 4.17 | | | |
| 13.0 | 312 | 0.54 | 0.54 | −0.020 | −1.8% | 1.19 | 1.19 | −0.080 | −3.3% |
| 13.0 | 313 | 1.99 | | | | 4.00 | | | |
| 13.5 | 324 | 0.53 | 0.53 | −0.020 | −1.9% | 1.15 | 1.15 | −0.080 | −3.4% |
| 13.5 | 325 | 1.86 | | | | 3.86 | | | |
| 14.0 | 336 | 0.51 | 0.51 | −0.040 | −3.8% | 1.10 | 1.10 | −0.100 | −4.3% |
| 14.0 | 337 | 1.84 | | | | 3.82 | | | |
| 14.5 | 348 | 0.50 | 0.50 | −0.020 | −2.0% | 1.07 | 1.07 | −0.060 | −2.7% |
| 14.5 | 349 | 1.70 | | | | 3.65 | | | |
| 15.0 | 360 | 0.48 | 0.48 | −0.040 | −4.0% | 1.03 | 1.03 | −0.080 | −3.7% |
| 15.0 | 361 | 1.68 | | | | 3.61 | | | |

Figure 4:
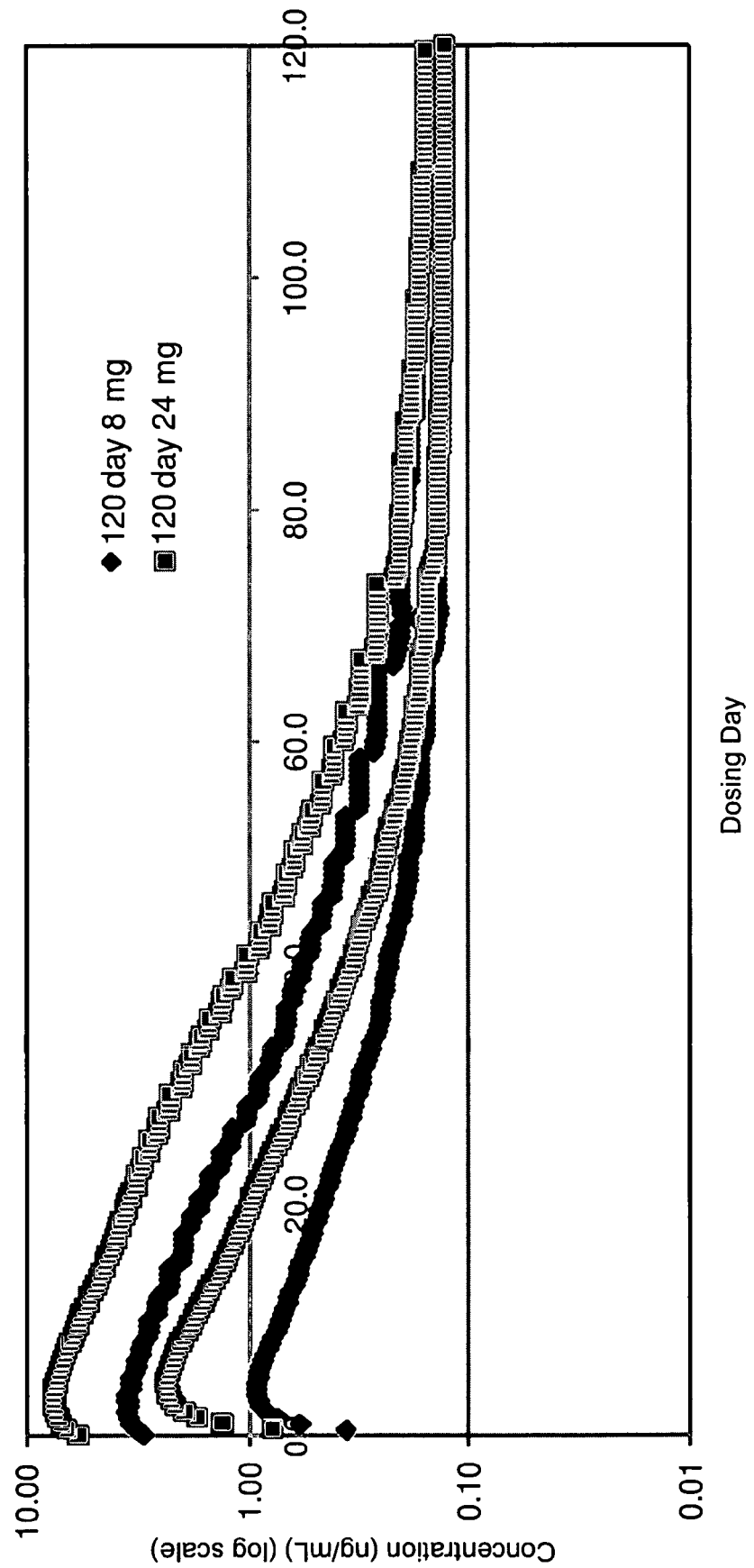
FIG. 4 is a graphic illustration of the dosage regimen data of the peak and lowest concentration of buprenorphine hydrochloride in the blood represented by Table 8 for a 120 day regimen and plotted in semi log form for a 120 day regimen.

Some of the data (the first 20 days of data of the 120 days) for the 8 mg and 24 mg is shown in Table 8 for the 120-day regimen while FIG. 4 shows a graphical illustration of all of the data showing the peak and lowest level concentrations for the 120-day regimen.

TABLE 8

| Dose Time (day) | Dose Time (hr) | Multidose 120 days ng/mL @8 mg | Trough ng/mL | Slope | Change from prev | Multidose 120 days ng/mL @24 mg | Trough ng/mL | Slope | Change from prev |
|---|---|---|---|---|---|---|---|---|---|
| 0.0 | 0 | 0.00 | 0.00 | | | 0.00 | 0.00 | | |
| 0.0 | 1 | 2.98 | | | | 5.90 | | | |
| 0.5 | 12 | 0.36 | 0.36 | | | 0.79 | 0.79 | | |
| 0.5 | 13 | 3.20 | | | | 6.58 | | | |
| 1.0 | 24 | 0.59 | 0.59 | | | 1.34 | 1.34 | | |
| 1.0 | 25 | 3.42 | | | | 7.03 | | | |
| 1.5 | 36 | 0.74 | 0.74 | | | 1.72 | 1.72 | | |
| 1.5 | 37 | 3.47 | | | | 7.28 | | | |
| 2.0 | 48 | 0.83 | 0.83 | | | 1.98 | 1.98 | | |
| 2.0 | 49 | 3.55 | | | | 7.53 | | | |
| 2.5 | 60 | 0.88 | 0.88 | | | 2.16 | 2.16 | | |
| 2.5 | 61 | 3.47 | | | | 7.59 | | | |
| 3.0 | 72 | 0.90 | 0.90 | | | 2.28 | 2.28 | | |
| 3.0 | 73 | 3.49 | | | | 7.63 | | | |
| 3.5 | 84 | 0.92 | 0.92 | | | 2.34 | 2.34 | | |
| 3.5 | 85 | 3.51 | | | | 7.62 | | | |
| 4.0 | 96 | 0.93 | 0.93 | | | 2.37 | 2.37 | | |
| 4.0 | 97 | 3.40 | | | | 7.58 | | | |
| 4.5 | 108 | 0.92 | 0.92 | −0.020 | −1.1% | 2.38 | 2.38 | | |
| 4.5 | 109 | 3.39 | | | | 7.42 | | | |
| 5.0 | 120 | 0.91 | 0.91 | −0.020 | −1.1% | 2.36 | 2.36 | −0.040 | −0.8% |
| 5.0 | 121 | 3.38 | | | | 7.31 | | | |
| 5.5 | 132 | 0.90 | 0.90 | −0.020 | −1.1% | 2.32 | 2.32 | −0.080 | −1.7% |
| 5.5 | 133 | 3.22 | | | | 7.19 | | | |

TABLE 8-continued

| Dose Time (day) | Dose Time (hr) | Multidose 120 days ng/mL @8 mg | Trough ng/mL | Slope | Change from prev | Multidose 120 days ng/mL @24 mg | Trough ng/mL | Slope | Change from prev |
|---|---|---|---|---|---|---|---|---|---|
| 6.0 | 144 | 0.88 | 0.88 | −0.040 | −2.2% | 2.28 | 2.28 | −0.080 | −1.7% |
| 6.0 | 145 | 3.20 | | | | 7.05 | | | |
| 6.5 | 156 | 0.86 | 0.86 | −0.040 | −2.3% | 2.23 | 2.23 | −0.100 | −2.2% |
| 6.5 | 157 | 3.18 | | | | 6.91 | | | |
| 7.0 | 168 | 0.85 | 0.85 | −0.020 | −1.2% | 2.18 | 2.18 | −0.100 | −2.2% |
| 7.0 | 169 | 3.06 | | | | 6.76 | | | |
| 7.5 | 180 | 0.82 | 0.82 | −0.060 | −3.5% | 2.12 | 2.12 | −0.120 | −2.8% |
| 7.5 | 181 | 3.03 | | | | 6.60 | | | |
| 8.0 | 192 | 0.80 | 0.80 | −0.040 | −2.4% | 2.06 | 2.06 | −0.120 | −2.8% |
| 8.0 | 193 | 3.01 | | | | 6.43 | | | |
| 8.5 | 204 | 0.78 | 0.78 | −0.040 | −2.5% | 2.00 | 2.00 | −0.120 | −2.9% |
| 8.5 | 205 | 2.86 | | | | 6.26 | | | |
| 9.0 | 216 | 0.75 | 0.75 | −0.060 | −3.8% | 1.93 | 1.93 | −0.140 | −3.5% |
| 9.0 | 217 | 2.83 | | | | 6.08 | | | |
| 9.5 | 228 | 0.73 | 0.73 | −0.040 | −2.7% | 1.86 | 1.86 | −0.140 | −3.6% |
| 9.5 | 229 | 2.81 | | | | 5.90 | | | |
| 10.0 | 240 | 0.72 | 0.72 | −0.020 | −1.4% | 1.80 | 1.80 | −0.120 | −3.2% |
| 10.0 | 241 | 2.80 | | | | 5.84 | | | |
| 10.5 | 252 | 0.71 | 0.71 | −0.020 | −1.4% | 1.75 | 1.75 | −0.100 | −2.8% |
| 10.5 | 253 | 2.61 | | | | 5.67 | | | |
| 11.0 | 264 | 0.69 | 0.69 | −0.040 | −2.8% | 1.70 | 1.70 | −0.100 | −2.9% |
| 11.0 | 265 | 2.58 | | | | 5.49 | | | |
| 11.5 | 276 | 0.67 | 0.67 | −0.040 | −2.9% | 1.64 | 1.64 | −0.120 | −3.5% |
| 11.5 | 277 | 2.57 | | | | 5.32 | | | |
| 12.0 | 288 | 0.66 | 0.66 | −0.020 | −1.5% | 1.59 | 1.59 | −0.100 | −3.0% |
| 12.0 | 289 | 2.56 | | | | 5.26 | | | |
| 12.5 | 300 | 0.65 | 0.65 | −0.020 | −1.5% | 1.54 | 1.54 | −0.100 | −3.1% |
| 12.5 | 301 | 2.33 | | | | 5.08 | | | |
| 13.0 | 312 | 0.63 | 0.63 | −0.040 | −3.1% | 1.49 | 1.49 | −0.100 | −3.2% |
| 13.0 | 313 | 2.31 | | | | 4.92 | | | |
| 13.5 | 324 | 0.61 | 0.61 | −0.040 | −3.2% | 1.44 | 1.44 | −0.100 | −3.4% |
| 13.5 | 325 | 2.29 | | | | 4.74 | | | |
| 14.0 | 336 | 0.60 | 0.60 | −0.020 | −1.6% | 1.39 | 1.39 | −0.100 | −3.5% |
| 14.0 | 337 | 2.28 | | | | 4.69 | | | |
| 14.5 | 348 | 0.59 | 0.59 | −0.020 | −1.7% | 1.35 | 1.35 | −0.080 | −2.9% |
| 14.5 | 349 | 2.27 | | | | 4.51 | | | |
| 15.0 | 360 | 0.59 | 0.59 | 0.000 | −0.0% | 1.31 | 1.31 | −0.080 | −3.0% |
| 15.0 | 361 | 2.04 | | | | 4.46 | | | |
| 15.5 | 372 | 0.57 | 0.57 | −0.040 | −3.4% | 1.28 | 1.28 | −0.060 | −2.3% |
| 15.5 | 373 | 2.02 | | | | 4.34 | | | |
| 16.0 | 384 | 0.55 | 0.55 | −0.040 | −3.5% | 1.24 | 1.24 | −0.080 | −3.1% |
| 16.0 | 385 | 2.00 | | | | 4.18 | | | |
| 16.5 | 396 | 0.54 | 0.54 | −0.020 | −1.8% | 1.20 | 1.20 | −0.080 | −3.2% |
| 16.5 | 397 | 1.99 | | | | 4.14 | | | |
| 17.0 | 408 | 0.53 | 0.53 | −0.020 | −1.9% | 1.17 | 1.17 | −0.060 | −2.5% |
| 17.0 | 409 | 1.98 | | | | 3.98 | | | |
| 17.5 | 420 | 0.52 | 0.52 | −0.020 | −1.9% | 1.13 | 1.13 | −0.080 | −3.4% |
| 17.5 | 421 | 1.97 | | | | 3.95 | | | |
| 18.0 | 432 | 0.51 | 0.51 | −0.020 | −1.9% | 1.11 | 1.11 | −0.040 | −1.8% |
| 18.0 | 433 | 1.84 | | | | 3.82 | | | |
| 18.5 | 444 | 0.50 | 0.50 | −0.020 | −2.0% | 1.07 | 1.07 | −0.080 | −3.6% |
| 18.5 | 445 | 1.83 | | | | 3.79 | | | |
| 19.0 | 456 | 0.49 | 0.49 | −0.020 | −2.0% | 1.05 | 1.05 | −0.040 | −1.9% |
| 19.0 | 457 | 1.82 | | | | 3.63 | | | |
| 19.5 | 468 | 0.48 | 0.48 | −0.020 | −2.0% | 1.02 | 1.02 | −0.060 | −2.9% |
| 19.5 | 469 | 1.69 | | | | 3.60 | | | |
| 20.0 | 480 | 0.47 | 0.47 | −0.020 | −2.1% | 0.99 | 0.99 | −0.060 | −2.9% |
| 20.0 | 481 | 1.67 | | | | 3.58 | | | |

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A method of treating opioid dependence while minimizing withdrawal symptoms, the method comprising:
providing an initial dosing regimen of buprenorphine or a pharmaceutically acceptable salt thereof, the initial dosing regimen being sufficient to minimize withdrawal symptoms wherein the initial dosing regimen has at least one predefined dosing period of at least two days with doses taken at least two times per day;
titrating a lowest concentration level of the buprenorphine or a pharmaceutically acceptable salt thereof in the blood at the end of the initial dosing regimen or immediately before a second or later dose of the initial dosing regimen is taken; and
providing a plurality of dosages of the buprenorphine or a pharmaceutically acceptable salt thereof plurality of subsequent dosing periods wherein each subsequent dosing period of the plurality of dosing periods is at least two days with doses taken at least two times per day and provides a dosing amount that is less than the dosing amount of the immediately preceding dosing period, the dosing amount in each subsequent dosing period providing a lowest concentration level in the blood of the buprenorphine or a pharmaceutically acceptable salt thereof for the associated dosing period that is equal to at least ninety-five percent of the lowest concentration in the blood of the buprenorphine or a pharmaceutically acceptable salt thereof of the immediately preceding dosing period and wherein the method extends for no less than sixty days.

2. The method of claim 1 wherein the plurality of subsequent dosing periods added together extends the method for ninety days or more.

3. The method of claim 1 wherein the plurality of subsequent dosing periods added together extends the method for one hundred twenty days or more.

4. A kit for treating opioid addiction while minimizing withdrawal symptoms, the kit comprising:
a plurality of dosage forms of buprenorphine or a pharmaceutically acceptable salt thereof the plurality of dosage forms being packaged in a plurality of decreasing dosing series, the plurality of dosage forms contains an initial dosing amount of buprenorphine or a pharmaceutically acceptable salt thereof for an initial dosing series sufficient to minimize withdrawal symptoms wherein the initial dosing series provides doses to be taken at least two times per day and for at least two days and a dosing amount of the buprenorphine or a pharmaceutically acceptable salt thereof in each subsequent decreasing dosing series provides doses to be taken at least two times per day and for at least two days that when administered ensures that the lowest concentration level in the blood of the buprenorphine or a pharmaceutically acceptable salt thereof for the subsequent dosing series is equal to at least ninety-five percent of the lowest concentration level in the blood of the immediately preceding dosing series and wherein the quantity of dosage forms is sufficient for administration for no less than sixty days; and
instructions to administer the initial dosing amount for an initial dosing series to minimize withdrawal symptoms, and to determine the lowest concentration level in the blood of the buprenorphine or a pharmaceutically acceptable salt thereof for the initial dosing series whereby the determined lowest concentration level in the blood of the initial dosing series is the value used for determining the subsequent lowest concentration value for the next subsequent dosing series to thereby provide a concentration in the blood for the next subsequent series that is at least ninety-five percent of the lowest concentration level in the blood of the previous dosing series.

5. The kit of claim 4 wherein the quantity of dosage forms is sufficient for administration for ninety days or more.

6. The kit of claim 4 wherein the quantity of dosage forms is sufficient for administration for one hundred twenty days or more.

7. A plurality of dosing regimens formulated for treating opioid addiction that provides for minimizing withdrawal symptoms, the plurality of dosing regimens comprising:
a quantity of buprenorphine or a pharmaceutically acceptable salt thereof contained in each of the plurality of dosing regimens wherein the plurality of dosing regimens includes an initial dosing regimen of at least two days with doses taken at least two times per day and a plurality of subsequent decreasing dosing regimens wherein each dosing regimen contains a dosing amount for at least two days with doses taken at least two times per day of the buprenorphine or a pharmaceutically acceptable salt thereof that when administered ensures that the lowest concentration level in the blood plasma of the buprenorphine or a pharmaceutically acceptable salt thereof for a subsequent dosing regimen is equal to at least ninety-five percent of the lowest concentration level in the blood plasma of the immediately preceding dosing regimen and wherein the quantity of the buprenorphine or a pharmaceutically acceptable salt thereof is sufficient for administration for no less than sixty days.

8. The plurality of dosing regimens of claim 7 wherein the quantity of the buprenorphine or a pharmaceutically acceptable salt thereof is sufficient for administration for ninety days or more.

9. The plurality of dosing regimens of claim 7 wherein the quantity of the buprenorphine or a pharmaceutically acceptable salt thereof is sufficient for administration for one hundred twenty days or more.

10. The method of claim 1 wherein the plurality of subsequent dosing periods added together extends the method for seventy days or more.

11. The kit of claim 4 wherein the quantity of dosage forms is sufficient for administration for seventy days or more.

12. The plurality of dosing regimens of claim 7 wherein the quantity of the buprenorphine or a pharmaceutically acceptable salt thereof is sufficient for administration for seventy days or more.

* * * * *

UNITED STATES PATENT AND TRADEMARK OFFICE
CERTIFICATE OF CORRECTION

| | | |
|---|---|---|
| PATENT NO. | : 8,163,731 B2 | Page 1 of 1 |
| APPLICATION NO. | : 12/195143 | |
| DATED | : April 24, 2012 | |
| INVENTOR(S) | : Kenneth C. Slater et al. | |

It is certified that error appears in the above-identified patent and that said Letters Patent is hereby corrected as shown below:

In the Claims

In column 26, claim 1, line 65, after "acceptable salt thereof" insert --for a--.

Signed and Sealed this
Tenth Day of July, 2012

David J. Kappos
*Director of the United States Patent and Trademark Office*